US006677454B2

(12) United States Patent
Babich et al.

(10) Patent No.: US 6,677,454 B2
(45) Date of Patent: Jan. 13, 2004

(54) IMAGING AGENTS FOR DIAGNOSIS OF PARKINSON'S DISEASE

(75) Inventors: John W. Babich, North Scituate, MA (US); Miles P. Smith, Belmont, MA (US)

(73) Assignee: Biostream Therapeutics, Inc., Cambridge, MA (US)

( * ) Notice: Subject to any disclaimer, the term of this patent is extended or adjusted under 35 U.S.C. 154(b) by 0 days.

(21) Appl. No.: 10/352,764

(22) Filed: Jan. 28, 2003

(65) Prior Publication Data

US 2003/0208078 A1 Nov. 6, 2003

Related U.S. Application Data

(62) Division of application No. 09/790,320, filed on Feb. 22, 2001, now Pat. No. 6,515,131.
(60) Provisional application No. 60/183,996, filed on Feb. 22, 2000.

(51) Int. Cl.$^7$ ............................................. C07D 211/60

(52) U.S. Cl. .................. 546/228; 546/227; 546/232; 546/233; 546/234; 546/194; 546/193

(58) Field of Search ................. 546/227, 228, 546/232, 233, 234, 194, 193

(56) References Cited

U.S. PATENT DOCUMENTS

| | | | | |
|---|---|---|---|---|
| 5,136,038 A | * | 8/1992 | Bodor | 546/169 |
| 5,143,854 A | | 9/1992 | Pirrung et al. | 436/518 |
| 5,288,514 A | | 2/1994 | Ellman | 427/2 |
| 5,359,115 A | | 10/1994 | Campbell et al. | 558/110 |
| 5,362,899 A | | 11/1994 | Campbell | 558/108 |
| 5,440,016 A | | 8/1995 | Blondelle et al. | 530/330 |
| 5,480,971 A | | 1/1996 | Houghten et al. | 530/328 |
| 5,919,934 A | | 7/1999 | John et al. | 546/247 |
| 6,171,576 B1 | | 1/2001 | Meltzer et al. | 424/1.65 |

FOREIGN PATENT DOCUMENTS

| | | | |
|---|---|---|---|
| EP | 0 200 211 A1 | | 11/1986 |
| WO | WO 91/07087 | | 5/1991 |
| WO | WO 92/10092 | | 6/1992 |
| WO | WO 93/09668 | | 5/1993 |
| WO | WO 93/20242 | | 10/1993 |
| WO | WO 94/08051 | | 4/1994 |
| WO | WO 98/37055 | | 8/1998 |
| WO | WO 01.83436 | * | 11/2001 |
| WO | WO 01/83436 A2 | | 11/2001 |
| WO | WO 01/98266 | | 12/2001 |

OTHER PUBLICATIONS

Innis et al.; "Single Photon Emission Computed Tomography Imaging of Monoamine Reuptake Sites in Primate Brain With [$^{123}$I] CIT", European Journal of Pharmacology 200, 369–370, (1991).

Kung et al.; "Imaging of Dopamine Transporters in Humans with Technetium–99m TRODAT–1", European Journal of Nuclear Medicine, 23 (11): 1527–1530, (1996).

Dahl et al.; "Deletion Mapping of X–Linked Mixed Deafness (DFN3) Identifies A 265–525–kb Region Centrometric of DXS26", Am. J. Hum. Genet. 56: 999–1002, (1995).

Valerio et al.; "Synthesis of Peptide analogues Using the Mutiplin Peptide Synthesis Method", Analytical Biochemistry 197: 168–177 (1991).

Stoof et al.; "Leads for the Development of Neuroprotective Treatment in Parkinson's Disease and Brain Imaging Methods for Estimating Treatment Efficacy", European Journal of Pharmacology 375:75–86, (1999).

Gallop et al.; "Application of Combinational Technologies to Drug Discovery. 1. Background and Peptide Combinatorial Libraries", Journal of Medicinal Chemistry, 37(9) : 1233–1251, (Apr. 29, 1994).

Berge et al.; "Pharmaceutical Salts", Journal of Pharmaceutical Sciences, 66(1): 1–19, (Jan. 1977).

Ohlmeyer et al.; "Complex Synthetic Chemical Libraries Indexed with Molecular Togs", Proc. Natl. Acad. Sci. USA, 90: 10922–10926, (Dec. 1993).

Innis et al.; "Single Photon Emission Computed Tomographic Imaging Demonstrates Loss of Striatal Dopamine Transporeters in Parkinson Disease", Proc. Natl. Acad. Sci. USA 90: 11965–11969, (Dec. 1993).

Kung et al.; "Synthesis of New Bis (Aminoethanethiol) (BAT) Derivatives: Possible Ligands for $^{99m}$Tc Brain Imaging Agents", J. Med. Chem. 28: 1280–1284, (1985).

Meltzer et al.; "Substituted 3–Phenyltropane Analogs oc Cocaine: Synthesis, Inhibition of Binding at Cocaine Recognition Sites, and Positron Emission Tomography Imaging", J.Med. Chem. 36: 855–862, (1993).

Carroll et al.; "Cocaine Receptor: Biochemical Characterization and Structure–Activity Relationships of Cocaine Analogues at the Dopamine Transporter", Journal of Medicinal Chemistry, 35(6): 969–981, (Mar. 20, 1992).

Meegalla et al.; "First Example of a $^{99m}$Tc Complex as a Dopamine Transporter Imaging Agent", J. Am. Chem. Soc. 117: 11037–11038, (1995).

Smith et al.; "Tuning Selectivity of Monomine Transporter Inhibitors by the Stereochemistry of the Nitrogen Lone Pair", J. Am. Chem. Soc. 120: 9072–9073, 9 1998).

(List continued on next page.)

Primary Examiner—Ceila Chang
(74) Attorney, Agent, or Firm—Dana M. Gordon; Foley Hoag LLP

(57) ABSTRACT

Generally, the present invention is directed to central nervous system dopamine transporter-imaging agents and methods of use thereof. In certain embodiments, the present invention relates to radiolabeled piperidine derivatives for use as imaging agents in the diagnosis of Parkinson's disease. Another aspect of the present invention relates to piperidine monoamine transporter ligands, comprising a functional group capable of chelating a radionuclide, e.g., technetium, and methods of use thereof.

14 Claims, No Drawings

OTHER PUBLICATIONS

Neumeyer et al.; "[$^{123}$] 2β–Carbometholoxy–3β–(-(4–iodophenyl) Tropane: High–Affinity SPECT Radiotracer of Monoamine Reuptake Sites in Brain", J. Med. Chem. 34 :3144–3146, (1991).

Hoepping et al.; "Synthesis and Biological of Two Novel Dat–Binding Technetium Complexes Containing a Piperidine Based Analogue of Cocaine", Bioorganic & Medicinal Chemistry Letters, 9: 3211–3216, (1999).

Gu et al.; "Stable Expression of Biogenic Amine Transporters Reveals Differences in Inhibitor Sensitivity, Kinetics, and Ion Dependence", The Journal of Biological Chemistry, 269 (10): 7124–7130,(1994).

Frost et al.; "Positron Emission Tomographic Imaging of the Dopamine Transporter with $^{11}$ C–WIN 35,428 Reveals Marked Declines in Mild Parkinson's Disease", Annals of Neurology, 34:423–431, (1993).

Blaney and Dixon, "Receptor Modeling by Distance Geometry", Annual Reports in Medicinal Chemistry, 26:281–286, (1991).

Meegalla et al.; "Synthesis and Characterization of Technetium–99–m–Labeled Tropanes as Dopamine Transporter–Imaging Agent", J. Med. Chem. 40: 9–17, (1997).

Hamilton and Steiner, "Immunophilins: Beyond Immunosuppression", Journal of Medicinal Chemistry, 41(26):5119–5143, (Dec. 17, 1998).

Luyt et al.; "An $N_2$ $S_2$ Bifunctional Chelator for Technetium–99m and Rhenium: Complexation, Conjugation, and Epimerization to a Single Isomer", Bioconjugate Chem. 10: 470–479, (1999).

Hom and katzenellenbogen; "Technetium–99m–Labeled Receptor–Specific Small–Molecule Radiopharmaceuticals: Recent Developments and Encouraging Results", Nuclear Medicine and Biology, 24: 485–498, (1997).

Nicholson et al.; "The Synthesis and Characterization of [MCI$_3$ (N= NC $_5$H$_4$ NH) (HN=NC$_5$ H$_4$ N) ] From [MO $_4$ ]$^-$ (where M= Re, Tc) Organodiazenido, Organodiazene–Chelate Complexes. The X–ray structure of [ReCl $_3$ (N=NC $_5$ H$_4$NH) (HN=NC$_5$H $_4$ N)]", Inorganica Chimica Acta, 252: 421–426, (1996).

Rose et al.; "Synthesis and Characterization of Organohydrazino Complexes of Technetium, Rhenium, and Molybdenum with the { M(η$^1$—H $_x$NNR)(η$^2$–H$_y$NNR)} Core and Their Relationship to Radiolabeled Organohydrazine–Derivatized Chemotactic Peptides with Diagnostic Applications", Inorg. Chem. 37: 2701–2716, (1998).

Fowler et al.; "Mapping Cocaine Binding Sites in Human and Baboon Brain In Vivo", Synapse, 4:371–377, (1989).

Villemagne et al.; "Doses of GBR12909 That Suppress Cocaine Self–Administration in Non—Human Primates Substantially Occupy Dopamine Transporters as Measured by [ 11 C ] WIN35,428 PET Scans", Synapse 32: 44–50, (1999).

Shaya et al.; "In Vivo Imaging of Dopamine Reuptake Sites in the Primate Brain Using Single Photon Emission Computer Tomography (SPECT) and Iodine–123 Labeled RTI–55", Synapse 10: 169–172 (1992).

Ilgin et al.; "PET Imaging of the Dopamine Transporter in Progressive Supranuclear Palsy and Parkinson's Disease", Neurology 52: 1221–1226, (1999).

Kaufman and Madras; "Distribution of Cocaine Recognition Sites in Monkey Brain: II. EX Vivo Autoradiography With [$^3$ H] CFT and [$^{125}$ I] RTI–55", Synapse 12: 99–111, (1992).

Jacobs and Fodor, "Combinatorial Chemistry– Applications of Light–directed Chemical Synthesis", TIBTECH. 12:19–26, (Jan. 1994).

Chen et al.; ""Analogous" Organic Synthesis of Small Compound Libraries: Validation of Combinatorial Chemistry in Small–Molecule Synthesis",J. Am. Chem. Soc. 116:2661–2662, (1994).

Kerr et al.; "Encoded Combinatorial Peptide Libraries Containing Non–Natural Amino Acids", J. Am. Chem. Soc. 115:2529–2531, (1993).

Kozikowski et al ;"Chemistry and Pharmacology of the Piperdine–Based Analogues of Cocaine. Identification of Potent DAT Inhibitors Lacking the Propane Skeleton", J. Med. Chem. 41: 1962–1969, (1998).

Patane et al.; "Selective α–1A Adrenergic Receptor Antagonists. Effects of Pharmacophore Regio–and Stereochemistry on Potency and Selectivity", Bioorganic and Medical Chemistry Letters 8:2595–2500, (1998).

Yung et al.; "In Vivo Dopamine Transporter Sites Imaging in Human Using [c–11] WIN 35,428 Position Emission Tomography (pet)", The Journal of Nuclear Medicine, 34(5): 197P(Abstract book), (May 1993).

Spies et al.; "Neutral Oxorhenium (v) Complexes with Tridentate Dithiolates and Monodentate Alkane– or Arene–thiolate Coligands", J. Chem Soc. Dalton Trans.; No. 13, pp. 2277–2280, (Jul. 7$^{th}$ , 1995).

Needels et al.; "Generation and Screening of an Oligonucleotide–encoded synthetic Peptide Library", Proc. Natl. Acad. Sci. USA 90: 10700–10704, (Nov. 1993).

Brenner and Lerner, "Encoded Combinatorial Chemistry", Proc. Natl. Acad. Sci. USA 89: 5381–5383, (Jun. 1992).

Bray et al.; "Gas Phase cleavage of Peptides from a Solid Support with Ammonia Vapour. Application in Simultaneous Multiple Peptide Synthesis", tetrahedron Letters 32(43): 6163–6166, (1991).

Bray et al.; "The Simultaneous Multiple Production of Solution Phase Peptides; Assessment of the Geysen Method of Symultaneous Peptide Synthesis", Tetrahedron Letters, 31 (40): 5811–5814, (Sep. 24, 1990).

Pátek and Lebl, "Safety–Catch anchoring Linkage for Synthesis of Peptide Amides by Boc/Fmoc Strategy", Tetrahedron Letters, 32 (31): 3891–3894 (Jul. 29, 1991).

Mitra–Kirtley; "Determination of the Nitrogen Chemical Structures in Petroleum Asphaltenes Using XANES Spectroscopy", J. Am. Chem. Soc. 115(1):252–258, (Jan. 13, 1993).

Geysen et al.; "Use of Peptide Synthesis to Probe Viral Antigens for Epitopes to a Resolution of a Single Amino Acid", Proc. Natl. Acad. Sci. USA 81(13):3998–4002, (Jul. 1984).

Houghten A. Richard, "General Method for the Rapid Solid–Phase Synthesis of Large Numbers of Peptides: Specificity of Antigen–Antibody Interaction at the Level of Individual Amino Acids", Proc. Natl. Acad. Sci., 82: 5131–5135, (Aug. 1985).

Hui et al.; "Analysis of the Quantitative Structure Activity Relationship of Technetium–99m–Labeled Diaminedithiol (DADT) and Propyleneamineoxine (PAO) Brain Blood Flow Analogues", Appl. Radiat. Isot. (International Journal of Radiation Applications: Part A). 42(6): 503–508, (1991).

Fodor et al.; "Light–Directed, Spatially Addressable Parallel Chemical Synthesis", Science, 251: 767–773, (Feb. 15, 1991).

Galli et al.; "Sodium– Dependent Norepinephrine–Induced Currents in Norepinephrine–Transporter–Transfected Hek–293 Cells Blocked by Cocaine and Antidepressants", The Journal of Experimental Biology, 198: 2197–2212, (1995).

Warren et al.; "New Iodinated Phenyl Fatty Acids For Imaging Myocardial Metabolism", The Journal of Nuclear Medicine 27(6): abstract No. 258, (Jun. 1986).

Mozley et al.; "Dosimetry of an Iodine–123–Labeled Tropane to Image Dopamine Transporters", J. Nucl. Med., 3791): 151–159, (Jan. 1996).

Nestler et al.; "A General Method for Molecular Tagging of Encoded Combinatorial Chemistry Libraries", J. Org. Chem. 59(17): 4723–4724.

Burbaum et al.; "A Paradigm for Drug Discovery Employing Encoded Combinatorial Libraries", Proc. Natl. Acad. Sci. USA, 92: 6027–6031, (Jun. 1995).

Efange et al.; "Synthesis and Biodistribution of 99 mTc Labeled Piperidinyl bis (Aminoethanethiol) Complexes: Potential Brain Perfusion Imaging Agents for Single Photon Emission Computed Tomography", CA 108: 167266 (1988).

* cited by examiner

IMAGING AGENTS FOR DIAGNOSIS OF PARKINSON'S DISEASE

RELATED APPLICATIONS

This application is a divisional of U.S. patent application Ser. No. 09/790,320, filed Feb. 22, 2001, now U.S. Pat. No. 6,515,131; which claims priority to U.S. Provisional Application for Patent serial No. 60/183,996, filed Feb. 22, 2000.

TECHNICAL FIELD

The present invention is directed to central nervous system dopamine transporter-imaging agents, and more particularly, to labeled piperidine derivatives for use as imaging agents in the diagnosis of Parkinson's disease.

BACKGROUND OF THE INVENTION

Each year approximately 50,000 Americans are diagnosed with Parkinson's disease with the estimated total cost to the US economy exceeding $5.6 billion annually. There exists no known test for Parkinson's Disease (PD) and current diagnosis relies on observations of the symptoms relating to deteriorating muscular control. With the difficulties in early diagnosis and no known causes, except for age or head trauma, the need for improved screening and treatment in our aging population continues to grow. While it has been demonstrated that disease progression can be monitored non-invasively in vivo by PET,[1,2] the inaccessibility and cost of PET make such screening ineffective. The availability of a radiolabeled dopamine transporter (DAT) ligand for imaging with single photon emission computed tomography (SPECT) would bring this capability to the majority of the population. Performing such brain imaging studies not only creates the possibility to follow the degeneration rate of the dopaminergic neurons in Parkinson's disease, but also provides an opportunity to estimate therapeutic effects of putative neuro-protective agents in individual patients.[3] Hence, an inexpensive and widely available agent for imaging DAT is warranted.

The development of radiolabeled ligands for SPECT imaging of the DAT has been difficult. Successful imaging of DAT in primates and humans has been demonstrated using several I-123-labeled analogs of the WIN 35,428 series of cocaine analogs.[4-6] However, the US market has yet to embrace Iodine-123 to the extent that there exists a commercially reliable and cost effective supply of this isotope. Tc-99m an inexpensive and more readily available isotope with ideal imaging characteristics for SPECT has enjoyed limited success as a radiolabel for DAT ligands. Kung et al, have demonstrated the technical feasibility of imaging DAT using TRODAT, a Tc-99m labeled tropane analog.[7,8] While a notable achievement, absolute brain uptake with this agent is very low resulting in less than ideal image quality. Structure activity studies to predict brain uptake with this series of ligands has proved to be less than reliable, suggesting the molecular size of the ligands is on the threshold for being able to cross the blood brain barrier efficiently. Kung et al have recently reported the dramatic effects of changes in the length of the carbon spacer unit in a tropane series of Tc-99m complexes.[9] Increasing the spacer length between the chelate and the tropane moeity from one to two carbons, while maintaining good transporter binding, resulted in little if any brain accumulation.

The National Parkinson's Foundation estimates that 1.5 million Americans are affected by Parkinson's disease (PD). While it is important to realize that PD is not a fatal disease, it is a crippling, degenerative disease with no cure. PD is a slowly progressive disease that affects a small area of cells located in the area of the brain known as the substantia nigra. The degeneration of these cells causes a reduction in a vital neurotransmitter involved in muscle activity (among other functions) called dopamine. The lack of dopamine causes a wide range of muscle misfunction but the four primary symptoms are tremors, rigidity, bradykinesia (slowness of movement) and postural instability. The disease is generally considered to target older adults, affecting 1 out of every 100 people over the age of 60.

Currently there is no known test available to diagnose a person with Parkinson's. The physician has to observe the symptoms until it is apparent that Parkinson's disease is present. Even with an experienced physician, an early, accurate diagnosis is difficult, especially with the many different forms of the disease, all treated with slightly different medications. The treatment of PD (the most common form of Parkinsonism) includes a delicate balance of medications, (usually the anticholinergic amantadine to start, follow by levodopa with cabidopa, Selegiline™, Bomocriptine™, or Perogolide™), allied health interventions (physical, occupational, and speech therapies) as well as new experimental procedures (thalamotomy to relieve tremors, Diacrin's fetal cell implants-NeuroCell™, or Guilford's neuroimmunophilin technology[11]). The list of medications for PD is extensive with all of the drug combinations possessing advantages and disadvantages. Evaluation is usually done on an individual basis in an attempt to minimize the potential side effects which include nausea, low blood pressure, involuntary movements, and restlessness, to name a few. The disease management is made more complex when one takes into account the "wearing-off" phenomenon and the "on-off" effects which commonly occur with these medications. With numerous drug combinations currently employed, countless new drugs coming through clinical trials (i.e. new dopamine agonists, Requip™ and Mirapex™), and the expense of new implantation procedures, it would be a great asset to be able to evaluate these potential treatments.

SUMMARY OF THE INVENTION

Generally, the present invention is directed to central nervous system dopamine transporter-imaging agents and methods of use thereof. In certain embodiments, the present invention relates to radiolabeled piperidine derivatives for use as imaging agents in the diagnosis of Parkinson's disease. Another aspect of the present invention relates to piperidine monoamine transporter ligands, comprising a functional group capable of chelating a radionuclide, e.g., technetium, and methods of use thereof.

DETAILED DESCRIPTION OF THE INVENTION

The main focus of our attention addresses the opportunity to improve detection and management of PD, we realize the other potential applications of our technology. Two other large potential markets concern cocaine abuse monitoring[12] and attention deficit hyperactivity disorders (ADHD/ADD). According to the National ADD Association millions of children (4–6% of the US population) are treated, and many overtreated, for the complex conditions of ADHD/ADD. The diagnostic criteria are lengthy and complex, often leading parents and doctors to clinically erroneous conclusions. We believe a definitive test would minimize the confusion, decrease unnecessary drug use, guide appropriate treatment, and monitor existing medications of the commonly prescribed Ritalin™, Dexedrine™, and Adderall™. The recent correlation established between ADD and mutations of the dopamine transporter gene[13] further demonstrates the need for a DAT-imaging agent.

One approach to developing new method for treatment of Parkinson's Disease involves investigating the piperidine nucleus, while maintaining the functional integrity of the system and the established chemistry of the $N_2S_2$ chelator. Based on our proprietary work we have developed the ability to rationally design DAT, SERT, and NET selective ligands by employing different isomeric forms, or other synthetic modifications.[10] Our proprietary position allows us to build upon the many recent successes in the field. Herein, we propose to synthesize and label a series of novel piperidine monoamine transporter ligands with technetium-99m, prepare the corresponding rhenium analogs, analyze their in vitro pharmacology, examine the in vivo localization properties, and evaluate their potential as specific tracers for the dopamine transport system. The new technetium imaging agents would improve initial diagnosis, as well as track the effects of potential therapeutic regiments in PD management.

In particular, one approach is to synthesize a series of novel piperidine monoamine transporter ligands, including separation and purification of all cis/trans isomers. Then prepare the corresponding rhenium-piperidine analogs, including separation, purification and structural identification of all syn/anti isomers. Subsequently, in vitro pharmacological studies can be performed on all piperidine ligands and the rhenium complexes. Thereafter, the 99mTc labeled versions of high affinity binding compounds defined in specific aim 3 can be prepared. Characterization of the technetium-labeled complexes by HPLC, and assessment of the complexes for their stability as a function of time and concentration, in buffer at physiological pH, and in human plasma and serum component may also be done Evaluation of the $^{99m}$Tc-complexes for brain uptake by performing in vivo rat studies may further be performed.

During this approach, the synthesis of the $N_2S_2$ derivatized piperidine ligands will be conducted along with the development of the Re/Tc-99m chemistry, analytical methods, and labeling techniques. The rhenium compounds will be prepared isomerically pure, to determine the structural identification, as well as the in vitro pharmacological profiles. Having assessed the initial rhenium compounds for selectivity of monoamine transporter binding, we will begin to develop the $^{99m}$Tc chemistry of the more promising ligands. Selection of lead compounds will be based on selectivity for the dopamine transporter versus the serotonin or norepinephrine transporter. The technetium-99m congeners will be evaluated initially for radiochemical purity and stability. Next, we will perform rat biodistribution studies, for assessment of brain uptake and retention analysis in the presence and absence of the DAT binding agent CFT. The sum of these endeavors will allow us to determine with reasonable certainty the feasibility of our approach for the development of DAT specific ligand for imaging. The results of the initial series can also serve to guide the synthesis of subsequent series of potential $^{99m}$Tc agents.

Once the above approach has been accomplished, the following approach may be pursued, for instance, in vivo imaging studies in non-human primates. In this approach, the following may be carried out: (i) validation of regioselective accumulation (substantia nigra) in non-human primate models using Tc-99m-complexes selected from specific aim 4 and single photon emission computed tomography (SPECT), (ii) determination of in vivo transporter selectivity by pharmacological challenge in non-human primates using transporter selective agents and single photon emission computed tomography (SPECT), and (iii) evaluation of the ability of the lead Tc-99m complex to image the "disease state" in a non-human primate as exemplified by unilateral lesions in the substantia nigra induced by the neurotoxin, MPTP. Subsequently, a "kit" for the preparation of the Tc-99m complex of the lead compound may be developed, and the radiation dosimetry of the Tc-99m complex of the lead compound may be assessed. Thereafter, the synthesis of the lead compound may be scaled up for: (i)PK and metabolism studies, (ii) assessment of the toxicity of the lead compound in two animal species, and (iii) expanded pharmacological studies of the Re-complex of the lead compound. Initiation of IND application preparation may be started.

Early diagnosis of PD is critical for the treatment and successful management of the disease. To address this issue we propose the development of our patented complexes into new easy to label $^{99m}$Tc-piperidine CNS imaging agents. Preparation of Tc-99m-CNS imaging agents would constitute a significant diagnostic and commercial opportunity in the ongoing battle against CNS related diseases such as Parkinson's disease.

Tc-99m, the most commonly used radionuclide in Nuclear Medicine, combines desirable physical properties with a 6 hr half-life and a 140-KeV gamma energy (85% as gamma photons) and widespread availability, since it can readily be eluted from molybdenum generators.[23] More than 85% of the radiotracers currently employed are labeled with Tc-99m.[24] These compelling criteria make Tc-99m the radionuclide of choice to radiolabel our series of piperidine ligands for targeting the DAT with SPECT.

There is a clear need for clinicians to be able to continually monitor the brain's DAT receptors in patients, to gather more information on (1) the etiopathogenesis, i.e., the cascade of events that ultimately leads to degeneration of the dopaminergic neurons, and (2) brain imaging methods, to estimate the extent of the degeneration of the dopaminergic neurons in the patient. This is not only important for the early diagnosis, but will also allow to monitor the effectiveness of alleged neuroprotective compounds on a prolonged basis. The development of a rapid non-invasive method to identify dopamine receptor activity is crucial to the understanding of PD and improving its diagnosis and treatment.

There is developed a method for preparing the cis and trans isomers of $^{99m}$Tc-piperidine complexes as radio probes for SPECT. Based on our previous work involving the three carbon spacer piperidine derivatives,[25] which demonstrated high binding affinities for the rhenium complexes at the DAT, we intend to explore other analogs. The complexes showed high binding affinities with the $K_i$ values ranging from 43–96 nM (using binding assays and [$^3$H]mazindol as the radioligand) but poor brain uptake. Combining our extensive SAR library with the work of Kung and coworkers[8,9] (where reduction of the carbon tether improved brain uptake), leads us to believe that our piperidine based system can maintain the successes of the past while improving upon the shortcomings, most notably brain uptake. Our system incorporates the cocaine-like functionality, the pendant $N_2S_2$ chelation off the 2β-position, and the carbon tether between the piperidine and $N_2S_2$ moiety. Moreover, our new complexes will be well under the molecular weight cutoff of the blood-brain-barrier, using the smaller chemical entity piperidine and a one carbon tether to the chelator, allowing for improved brain uptake.

In regards to the chelation of the metal center (Tc or Re) to the piperidine derivatives, keeping in mind the criteria of stability, predictability, neutrality, and very little perturbation on the system, we utilize the well established $N_2S_2$ system to provide a robust, neutral metal(V)-oxo core. We propose synthesizing a pendant $N_2S_2$ core. Whereas in the past the $N_2S_2$ derivatives were prepared without regard to charge potential, we have specifically designed our $N_2S_2$ chelator to possess a formal 3-charge. Therefore, upon addition of the metal-oxo (3+) core, the overall charge remains predictably neutral. Using the neutral diamninodithiol analogs, of the type shown in schemes 1–4, has a number of advantages: a) the piperidine moiety is free and remote from the Tc-99m chelation site, b) the product is neutral and is expected to retain the general properties of a cocaine analog, c) derivatives of diaminodithiol have proven to be good ligands for chelating Tc-99m at room temperature with high radiochemical yield and radiochemical purity, d) the ligand core keeps the metal in a favored +5 oxidation state, and finally e) the size of the Tc-99m-diaminodithio chelate is similar to that of the phenyl group,[26] which should not be detrimental to the binding. Another advantage of using this chelating strategy is that the $N_2S_2$ position on the molecule can be altered if necessary in order to determine its optimal location.

We have recently prepared the initial analog in this series via the route shown below in Scheme 1. This synthesis commenced with the piperidine ester 1, that is readily prepared from arecoline in two steps as reported in the literature.[8] The ester was hydrolysed and the resulting acid was then converted to the corresponding acid chloride 2 with oxalyl chloride in dichloromethane. Initial attempts to acylate the protected $N_2S_2$ chelate directly with 2 failed.

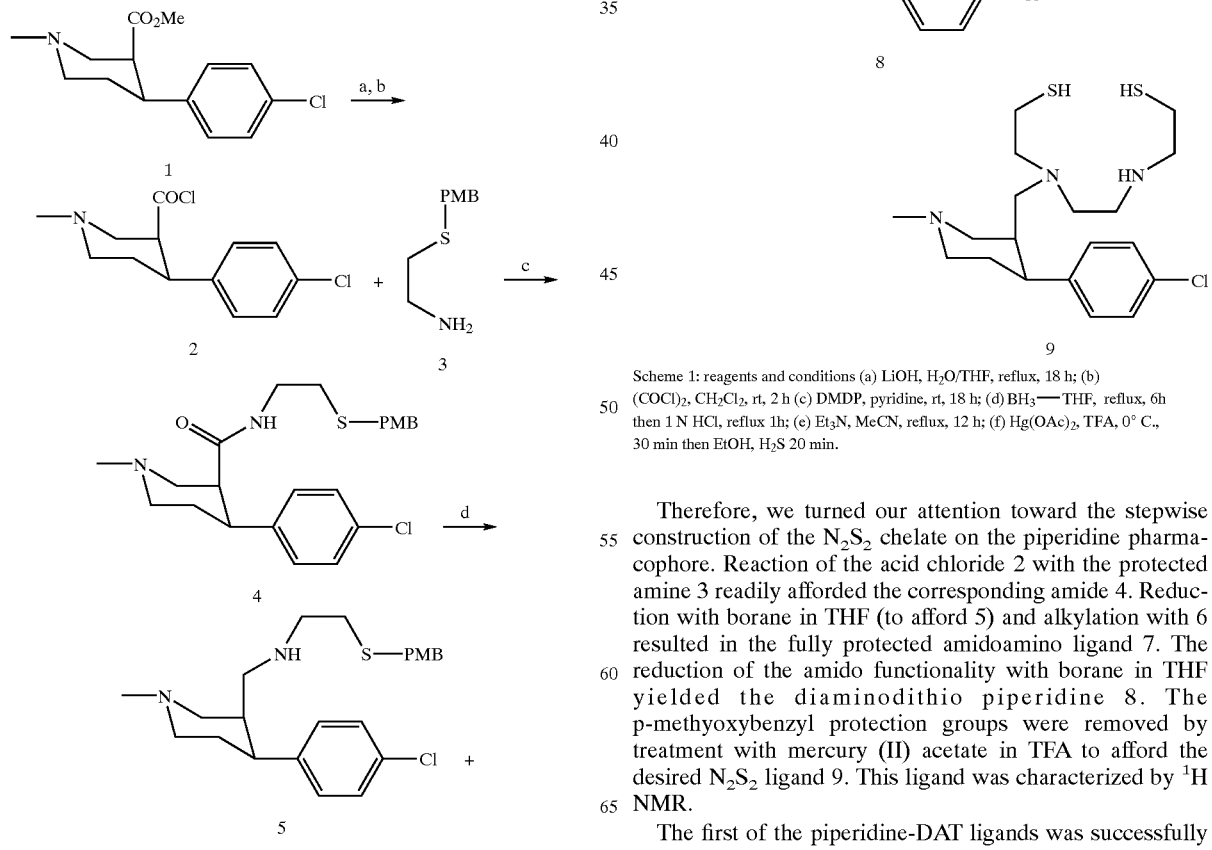

Scheme 1: reagents and conditions (a) LiOH, H₂O/THF, reflux, 18 h; (b) (COCl)₂, CH₂Cl₂, rt, 2 h (c) DMDP, pyridine, rt, 18 h; (d) BH₃—THF, reflux, 6h then 1 N HCl, reflux 1h; (e) Et₃N, MeCN, reflux, 12 h; (f) Hg(OAc)₂, TFA, 0° C., 30 min then EtOH, H₂S 20 min.

Therefore, we turned our attention toward the stepwise construction of the $N_2S_2$ chelate on the piperidine pharmacophore. Reaction of the acid chloride 2 with the protected amine 3 readily afforded the corresponding amide 4. Reduction with borane in THF (to afford 5) and alkylation with 6 resulted in the fully protected amidoamino ligand 7. The reduction of the amido functionality with borane in THF yielded the diaminodithio piperidine 8. The p-methyoxybenzyl protection groups were removed by treatment with mercury (II) acetate in TFA to afford the desired $N_2S_2$ ligand 9. This ligand was characterized by $^1$H NMR.

The first of the piperidine-DAT ligands was successfully labeled with Tc-99m by a trans chelation reaction with Tc-99m gluconate. The product was extracted into ethyl acetate and evaluated by HPLC: Hamilton PRP-1 column eluted with dimethylglutamic acid buffer and acetonitrile. The method applied was a gradient from 10–60% acetonitrile. In the HPLC system used the $^{99m}$Tc-piperidine complex eluted at 13 minutes whereas the precursor eluted at 3 minutes. Radiochemical yield was ~50%, with radiochemical purity >95%.

While the main focus of our attention addresses the opportunity to improve detection and management of PD, we realize the other potential applications of our technology. Two other large potential markets concern cocaine abuse monitoring[12] and attention deficit hyperactivity disorders (ADHD/ADD). According to the National ADD Association millions of children (4–6% of the US population) are treated, and many overtreated, for the complex conditions of ADHD/ADD. The diagnostic criteria are lengthy and complex, often leading parents and doctors to clinically erroneous conclusions. We believe a definitive test would minimize the confusion, decrease unnecessary drug use, guide appropriate treatment, and monitor existing medications of the commonly prescribed Ritalin™, Dexedrine™, and Adderall™. The recent correlation established between ADD and mutations of the dopamine transporter gene[13] further demonstrates the need for a DAT-imaging agent.

Neurotransmitter receptors and transporters are currently explored using positron emission tomography (PET). A recent study indicated that the normal ≧85% loss in dopamine innervation to the striatum necessary for clinical symptoms of PD, 50–60% reduction in dopaminergic tone can be detected using PET ligands [$^{11}$C] 2β-carbomethoxy-3-β-aryltropane and [$^{18}$F] 6-fluoro-DOPA. In recent years, imaging of CNS dopamine transporters using positron emission tomography (PET) and single-photon emission computed tomography (SPECT) has been demonstrated. Most of the radiopharmaceuticals that have been employed for the non-invasive measurement of dopamine transporter sites are based on the structure of the classical reuptake inhibitor, cocaine.[14] Cocaine itself has been used as a PET ligand and as expected concentrates in the basal gangia where dopamine terminal density is high.[15] Cocaine analogs with higher binding affinity for dopamine transporter sites and more favorable pharmacokinetic properties (due to slower metabolism) have been developed. Several of these ligands include [$^{11}$C] CFT (2β-carbomethoxy-3β-(4-fluorophenyl)tropane)[16] and [$^{11}$C] methylphenidate[17] for PET, and [$^{123}$I] β-CIT (2β-carbomethoxy-3β-(4-iodo-phenyl)tropane[18], [$^{123}$I]IPT (N-(3-iodopropen-2-yl)-2β-carbomethoxy-3β-(4-chlorophenyl)tropane)[19] and [$^{99m}$Tc]TRODAT-1[20] for SPECT imaging. While PET/SPECT scanning is currently the scientists best tool in potentially leading to improved treatment of Parkinson's disease, the present methods have shortcomings. The operation of PET requires access to a cyclotron, with cost and complexity precluding wide application at this time. The iodinated ligands, while proven to work, currently suffer from the markets lack of acceptance of I-123 as a viable tracer. Meanwhile, the brain uptake of the Tc-99m-SPECT complexes seriously limit their effectiveness. Other problems have also occurred in regards to the transporter selectivity of still other compounds.[21,22]

COMPOUNDS AND METHODS OF THE PRESENT INVENTION

In certain embodiments, a compound of the present invention is represented by A:

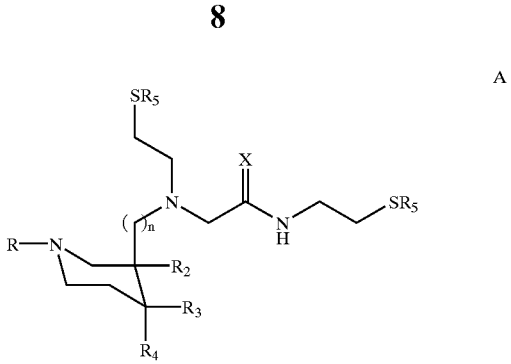

wherein
X represents O or (H)$_2$;
R represents H, alkyl, alkoxyl, alkylamino, aryl, heteroaryl, aralkyl, heteroaralkyl, acyl, alkoxycarbonyl, or alkylaminocarbonyl;
R$_2$ represents H;
R$_3$ represents optionally substituted aryl or heteroaryl;
R$_4$ represents H;
R$_5$ represents independently for each occurrence H, alkyl, alkoxyl, alkylamino, aryl, heteroaryl, aralkyl, heteroaralkyl, acyl, alkoxycarbonyl, or alkylaminocarbonyl; and
n is 0, 1, or 2.

In certain embodiments, a compound of the present invention is represented by A and the attendant definitions, wherein X represents O.

In certain embodiments, a compound of the present invention is represented by A and the attendant definitions, wherein R represents alkyl.

In certain embodiments, a compound of the present invention is represented by A and the attendant definitions, wherein R$_3$ represents optionally substituted phenyl.

In certain embodiments, a compound of the present invention is represented by A and the attendant definitions, wherein R$_5$ represents H or aralkyl.

In certain embodiments, a compound of the present invention is represented by A and the attendant definitions, wherein n is 1.

In certain embodiments, a compound of the present invention is represented by A and the attendant definitions, wherein X represents O; and R represents alkyl.

In certain embodiments, a compound of the present invention is represented by A and the attendant definitions, wherein X represents O; and R$_3$ represents optionally substituted phenyl.

In certain embodiments, a compound of the present invention is represented by A and the attendant definitions, wherein X represents O; and R$_5$ represents independently for each occurrence H or aralkyl.

In certain embodiments, a compound of the present invention is represented by A and the attendant definitions, wherein X represents O; and n is 1.

In certain embodiments, a compound of the present invention is represented by A and the attendant definitions, wherein X represents O; R represents alkyl; and R$_3$ represents optionally substituted phenyl.

In certain embodiments, a compound of the present invention is represented by A and the attendant definitions, wherein X represents O; R represents alkyl; and R$_5$ represents independently for each occurrence H or aralkyl.

In certain embodiments, a compound of the present invention is represented by A and the attendant definitions, wherein X represents O; R represents alkyl; R₃ represents optionally substituted phenyl; and R₅ represents independently for each occurrence H or aralkyl.

In certain embodiments, a compound of the present invention is represented by A and the attendant definitions, wherein X represents O; R represents methyl; R₃ represents 4-chlorophenyl; R₅ represents independently for each occurrence H or 4-methoxybenzyl; and n is 1.

In certain embodiments, a compound of the present invention is represented by B:

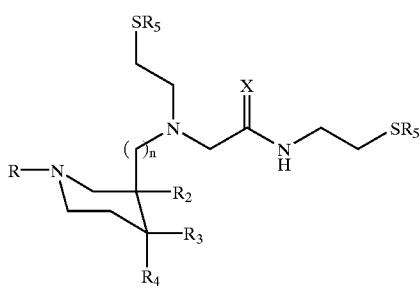

B wherein
- X represents O or (H)₂;
- R represents H, alkyl, alkoxyl, alkylamino, aryl, heteroaryl, aralkyl, heteroaralkyl, acyl, alkoxycarbonyl, or alkylaminocarbonyl;
- R₂ represents H;
- R₃ represents H;
- R₄ represents optionally substituted aryl or heteroaryl;
- R₅ represents independently for each occurrence H, alkyl, alkoxyl, alkylamino, aryl, heteroaryl, aralkyl, heteroaralkyl, acyl, alkoxycarbonyl, or alkylaminocarbonyl; and
- n is 0, 1, or 2.

In certain embodiments, a compound of the present invention is represented by B and the attendant definitions, wherein X represents O.

In certain embodiments, a compound of the present invention is represented by B and the attendant definitions, wherein R represents alkyl.

In certain embodiments, a compound of the present invention is represented by B and the attendant definitions, wherein R₄ represents optionally substituted phenyl.

In certain embodiments, a compound of the present invention is represented by B and the attendant definitions, wherein R₅ represents H or aralkyl.

In certain embodiments, a compound of the present invention is represented by B and the attendant definitions, wherein n is 1.

In certain embodiments, a compound of the present invention is represented by B and the attendant definitions, wherein X represents O; and R represents alkyl.

In certain embodiments, a compound of the present invention is represented by B and the attendant definitions, wherein X represents O; and R₄ represents optionally substituted phenyl.

In certain embodiments, a compound of the present invention is represented by B and the attendant definitions, wherein X represents O; and R₅ represents independently for each occurrence H or aralkyl.

In certain embodiments, a compound of the present invention is represented by B and the attendant definitions, wherein X represents O; and n is 1.

In certain embodiments, a compound of the present invention is represented by B and the attendant definitions, wherein X represents O; R represents alkyl; and R₄ represents optionally substituted phenyl.

In certain embodiments, a compound of the present invention is represented by B and the attendant definitions, wherein X represents O; R represents alkyl; and R₅ represents independently for each occurrence H or aralkyl.

In certain embodiments, a compound of the present invention is represented by B and the attendant definitions, wherein X represents O; R represents alkyl; R₄ represents optionally substituted phenyl; and R₅ represents independently for each occurrence H or aralkyl.

In certain embodiments, a compound of the present invention is represented by B and the attendant definitions, wherein X represents O; R represents methyl; R₄ represents 4-chlorophenyl; R₅ represents independently for each occurrence H or 4-methoxybenzyl; and n is 1.

In certain embodiments, a compound of the present invention is represented by C:

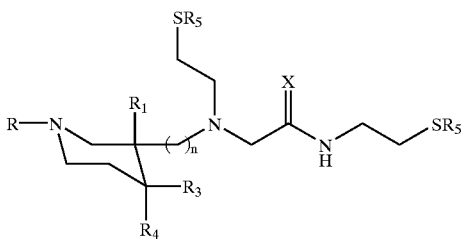

C wherein
- X represents O or (H)₂;
- R represents H, alkyl, alkoxyl, alkylamino, aryl, heteroaryl, aralkyl, heteroaralkyl, acyl, alkoxycarbonyl, or alkylaminocarbonyl;
- R₁ represents H;
- R₃ represents optionally substituted aryl or heteroaryl;
- R₄ represents H;
- R₅ represents independently for each occurrence H, alkyl, alkoxyl, alkylamino, aryl, heteroaryl, aralkyl, heteroaralkyl, acyl, alkoxycarbonyl, or alkylaminocarbonyl; and
- n is 0, 1, or 2.

In certain embodiments, a compound of the present invention is represented by C and the attendant definitions, wherein X represents O.

In certain embodiments, a compound of the present invention is represented by C and the attendant definitions, wherein R represents alkyl.

In certain embodiments, a compound of the present invention is represented by C and the attendant definitions, wherein R₃ represents optionally substituted phenyl.

In certain embodiments, a compound of the present invention is represented by C and the attendant definitions, wherein R₅ represents H or aralkyl.

In certain embodiments, a compound of the present invention is represented by C and the attendant definitions, wherein n is 1.

In certain embodiments, a compound of the present invention is represented by C and the attendant definitions, wherein X represents O; and R represents alkyl.

In certain embodiments, a compound of the present invention is represented by C and the attendant definitions, wherein X represents O; and R₃ represents optionally substituted phenyl.

In certain embodiments, a compound of the present invention is represented by C and the attendant definitions, wherein X represents O; and R₅ represents independently for each occurrence H or aralkyl.

In certain embodiments, a compound of the present invention is represented by C and the attendant definitions, wherein X represents O; and n is 1.

In certain embodiments, a compound of the present invention is represented by C and the attendant definitions, wherein X represents O; R represents alkyl; and R₃ represents optionally substituted phenyl.

In certain embodiments, a compound of the present invention is represented by C and the attendant definitions, wherein X represents O; R represents alkyl; and R₅ represents independently for each occurrence H or aralkyl.

In certain embodiments, a compound of the present invention is represented by C and the attendant definitions, wherein X represents O; R represents alkyl; R₃ represents optionally substituted phenyl; and R₅ represents independently for each occurrence H or aralkyl.

In certain embodiments, a compound of the present invention is represented by C and the attendant definitions, wherein X represents O; R represents methyl; R₃ represents 4-chlorophenyl; R₅ represents independently for each occurrence H or 4-methoxybenzyl; and n is 1.

In certain embodiments, a compound of the present invention is represented by D:

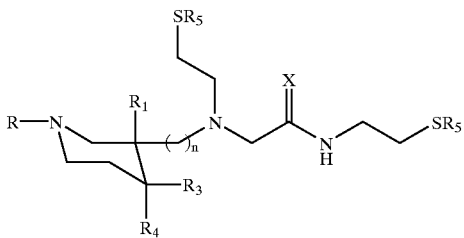

wherein
X represents O or (H)₂;
R represents H, alkyl, alkoxyl, alkylamino, aryl, heteroaryl, aralkyl, heteroaralkyl, acyl, alkoxycarbonyl, or alkylaminocarbonyl;
R₁ represents H;
R₃ represents H;
R₄ represents optionally substituted aryl or heteroaryl;
R₅ represents independently for each occurrence H, alkyl, alkoxyl, alkylamino, aryl, heteroaryl, aralkyl, heteroaralkyl, acyl, alkoxycarbonyl, or alkylaminocarbonyl; and
n is 0, 1, or 2.

In certain embodiments, a compound of the present invention is represented by D and the attendant definitions, wherein X represents O.

In certain embodiments, a compound of the present invention is represented by D and the attendant definitions, wherein R represents alkyl.

In certain embodiments, a compound of the present invention is represented by D and the attendant definitions, wherein R₄ represents optionally substituted phenyl.

In certain embodiments, a compound of the present invention is represented by D and the attendant definitions, wherein R₅ represents H or aralkyl.

In certain embodiments, a compound of the present invention is represented by D and the attendant definitions, wherein n is 1.

In certain embodiments, a compound of the present invention is represented by D and the attendant definitions, wherein X represents O; and R represents alkyl.

In certain embodiments, a compound of the present invention is represented by D and the attendant definitions, wherein X represents O; and R₄ represents optionally substituted phenyl.

In certain embodiments, a compound of the present invention is represented by D and the attendant definitions, wherein X represents O; and R₅ represents independently for each occurrence H or aralkyl.

In certain embodiments, a compound of the present invention is represented by D and the attendant definitions, wherein X represents O; and n is 1.

In certain embodiments, a compound of the present invention is represented by D and the attendant definitions, wherein X represents O; R represents alkyl; and R₄ represents optionally substituted phenyl.

In certain embodiments, a compound of the present invention is represented by D and the attendant definitions, wherein X represents O; R represents alkyl; and R₅ represents independently for each occurrence H or aralkyl.

In certain embodiments, a compound of the present invention is represented by D and the attendant definitions, wherein X represents O; R represents alkyl; R₄ represents optionally substituted phenyl; and R₅ represents independently for each occurrence H or aralkyl.

In certain embodiments, a compound of the present invention is represented by D and the attendant definitions, wherein X represents O; R represents methyl; R₄ represents 4-chlorophenyl; R₅ represents independently for each occurrence H or 4-methoxybenzyl; and n is 1.

In certain embodiments, a compound of the present invention is represented by E:

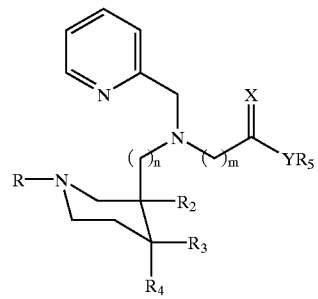

wherein
X represents O or S;
Y represents O or S;
R represents H, alkyl, alkoxyl, alkylamino, aryl, heteroaryl, aralkyl, heteroaralkyl, acyl, alkoxycarbonyl, or alkylaminocarbonyl;
R₂ represents H;
R₃ represents optionally substituted aryl or heteroaryl;
R₄ represents H;
R₅ represents H, alkyl, alkoxyl, alkylamino, aryl, heteroaryl, aralkyl, heteroaralkyl, acyl, alkoxycarbonyl, or alkylaminocarbonyl;
m is 1 or 2; and
n is 0, 1, or 2.

In certain embodiments, a compound of the present invention is represented by E and the attendant definitions, wherein X represents O.

In certain embodiments, a compound of the present invention is represented by E and the attendant definitions, wherein Y represents O.

In certain embodiments, a compound of the present invention is represented by E and the attendant definitions, wherein R represents alkyl.

In certain embodiments, a compound of the present invention is represented by E and the attendant definitions, wherein R₃ represents optionally substituted phenyl.

In certain embodiments, a compound of the present invention is represented by E and the attendant definitions, wherein R₅ represents H, alkyl, or aralkyl.

In certain embodiments, a compound of the present invention is represented by E and the attendant definitions, wherein m is 1.

In certain embodiments, a compound of the present invention is represented by E and the attendant definitions, wherein n is 1.

In certain embodiments, a compound of the present invention is represented by E and the attendant definitions, wherein X represents O; and Y represents O.

In certain embodiments, a compound of the present invention is represented by E and the attendant definitions, wherein X represents O; and R represents alkyl.

In certain embodiments, a compound of the present invention is represented by E and the attendant definitions, wherein X represents O; and R₃ represents optionally substituted phenyl.

In certain embodiments, a compound of the present invention is represented by E and the attendant definitions, wherein X represents O; and R₅ represents H, alkyl, or aralkyl.

In certain embodiments, a compound of the present invention is represented by E and the attendant definitions, wherein X represents O; and m is 1.

In certain embodiments, a compound of the present invention is represented by E and the attendant definitions, wherein X represents O; and n is 1.

In certain embodiments, a compound of the present invention is represented by E and the attendant definitions, wherein X represents O; Y represents O; R represents alkyl; and R₃ represents optionally substituted phenyl.

In certain embodiments, a compound of the present invention is represented by E and the attendant definitions, wherein X represents O; Y represents O; R represents alkyl; and R₅ represents H, alkyl, or aralkyl.

In certain embodiments, a compound of the present invention is represented by E and the attendant definitions, wherein X represents O; Y represents O; R represents alkyl; R₃ represents optionally substituted phenyl; and R₅ represents H, alkyl, or aralkyl.

In certain embodiments, a compound of the present invention is represented by E and the attendant definitions, wherein X represents O; Y represents O; R represents methyl; R₃ represents 4-chlorophenyl; R₅ represents ethyl; m is 1; and n is 1.

In certain embodiments, a compound of the present invention is represented by F:

F wherein
X represents O or S;
Y represents O or S;
R represents H, alkyl, alkoxyl, alkylamino, aryl, heteroaryl, aralkyl, heteroaralkyl, acyl, alkoxycarbonyl, or alkylaminocarbonyl;
R₂ represents H;
R₃ represents H;
R₄ represents optionally substituted aryl or heteroaryl;
R₅ represents H, alkyl, alkoxyl, alkylamino, aryl, heteroaryl, aralkyl, heteroaralkyl, acyl, alkoxycarbonyl, or alkylaminocarbonyl;
m is 1 or 2; and
n is 0, 1, or 2.

In certain embodiments, a compound of the present invention is represented by F and the attendant definitions, wherein X represents O.

In certain embodiments, a compound of the present invention is represented by F and the attendant definitions, wherein Y represents O.

In certain embodiments, a compound of the present invention is represented by F and the attendant definitions, wherein R represents alkyl.

In certain embodiments, a compound of the present invention is represented by F and the attendant definitions, wherein R₄ represents optionally substituted phenyl.

In certain embodiments, a compound of the present invention is represented by F and the attendant definitions, wherein R₅ represents H, alkyl, or aralkyl.

In certain embodiments, a compound of the present invention is represented by F and the attendant definitions, wherein m is 1.

In certain embodiments, a compound of the present invention is represented by F and the attendant definitions, wherein n is 1.

In certain embodiments, a compound of the present invention is represented by F and the attendant definitions, wherein X represents O; and Y represents O.

In certain embodiments, a compound of the present invention is represented by F and the attendant definitions, wherein X represents O; and R represents alkyl.

In certain embodiments, a compound of the present invention is represented by F and the attendant definitions, wherein X represents O; and R₄ represents optionally substituted phenyl.

In certain embodiments, a compound of the present invention is represented by F and the attendant definitions, wherein X represents O; and R₅ represents H, alkyl, or aralkyl.

In certain embodiments, a compound of the present invention is represented by F and the attendant definitions, wherein X represents O; and m is 1.

In certain embodiments, a compound of the present invention is represented by F and the attendant definitions, wherein X represents O; and n is 1.

In certain embodiments, a compound of the present invention is represented by F and the attendant definitions, wherein X represents O; Y represents O; R represents alkyl; and R$_4$ represents optionally substituted phenyl.

In certain embodiments, a compound of the present invention is represented by F and the attendant definitions, wherein X represents O; Y represents O; R represents alkyl; and R$_5$ represents H, alkyl, or aralkyl.

In certain embodiments, a compound of the present invention is represented by F and the attendant definitions, wherein X represents O; Y represents O; R represents alkyl; R$_4$ represents optionally substituted phenyl; and R$_5$ represents H, alkyl, or aralkyl.

In certain embodiments, a compound of the present invention is represented by F and the attendant definitions, wherein X represents O; Y represents O; R represents methyl; R$_4$ represents 4-chlorophenyl; R$_5$ represents ethyl; m is 1; and n is 1.

In certain embodiments, a compound of the present invention is represented by G:

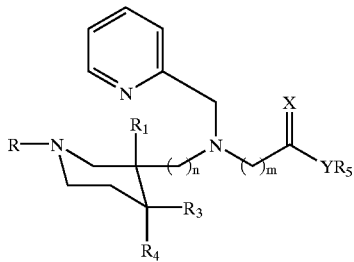

G wherein

X represents O or S;

Y represents O or S;

R represents H, alkyl, alkoxyl, alkylamino, aryl, heteroaryl, aralkyl, heteroaralkyl, acyl, alkoxycarbonyl, or alkylaminocarbonyl;

R$_1$ represents H;

R$_3$ represents optionally substituted aryl or heteroaryl;

R$_4$ represents H;

R$_5$ represents H, alkyl, alkoxyl, alkylamino, aryl, heteroaryl, aralkyl, heteroaralkyl, acyl, alkoxycarbonyl, or alkylaminocarbonyl;

m is 1 or 2; and n is 0, 1, or 2.

In certain embodiments, a compound of the present invention is represented by G and the attendant definitions, wherein X represents O.

In certain embodiments, a compound of the present invention is represented by G and the attendant definitions, wherein Y represents O.

In certain embodiments, a compound of the present invention is represented by G and the attendant definitions, wherein R represents alkyl.

In certain embodiments, a compound of the present invention is represented by G and the attendant definitions, wherein R$_3$ represents optionally substituted phenyl.

In certain embodiments, a compound of the present invention is represented by G and the attendant definitions, wherein R$_5$ represents H, alkyl, or aralkyl.

In certain embodiments, a compound of the present invention is represented by G and the attendant definitions, wherein m is 1.

In certain embodiments, a compound of the present invention is represented by G and the attendant definitions, wherein n is 1.

In certain embodiments, a compound of the present invention is represented by G and the attendant definitions, wherein X represents O; and Y represents O.

In certain embodiments, a compound of the present invention is represented by G and the attendant definitions, wherein X represents O; and R represents alkyl.

In certain embodiments, a compound of the present invention is represented by G and the attendant definitions, wherein X represents O; and R$_3$ represents optionally substituted phenyl.

In certain embodiments, a compound of the present invention is represented by G and the attendant definitions, wherein X represents O; and R$_5$ represents H, alkyl, or aralkyl.

In certain embodiments, a compound of the present invention is represented by G and the attendant definitions, wherein X represents O; and m is 1.

In certain embodiments, a compound of the present invention is represented by G and the attendant definitions, wherein X represents O; and n is 1.

In certain embodiments, a compound of the present invention is represented by G and the attendant definitions, wherein X represents O; Y represents O; R represents alkyl; and R$_3$ represents optionally substituted phenyl.

In certain embodiments, a compound of the present invention is represented by G and the attendant definitions, wherein X represents O; Y represents O; R represents alkyl; and R$_5$ represents H, alkyl, or aralkyl.

In certain embodiments, a compound of the present invention is represented by G and the attendant definitions, wherein X represents O; Y represents O; R represents alkyl; R$_3$ represents optionally substituted phenyl; and R$_5$ represents H, alkyl, or aralkyl.

In certain embodiments, a compound of the present invention is represented by G and the attendant definitions, wherein X represents O; Y represents O; R represents methyl; R$_3$ represents 4-chlorophenyl; R$_5$ represents ethyl; m is 1; and n is 1.

In certain embodiments, a compound of the present invention is represented by H:

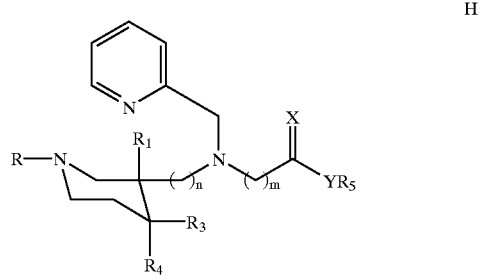

H wherein

X represents O or S;

Y represents O or S;

R represents H, alkyl, alkoxyl, alkylamino, aryl, heteroaryl, aralkyl, heteroaralkyl, acyl, alkoxycarbonyl, or alkylaminocarbonyl;

R$_1$ represents H;

R₃ represents H;
R₄ represents optionally substituted aryl or heteroaryl;
R₅ represents H, alkyl, alkoxyl, alkylamino, aryl, heteroaryl, aralkyl, heteroaralkyl, acyl, alkoxycarbonyl, or alkylaminocarbonyl;
m is 1 or 2; and
n is 0, 1, or 2.

In certain embodiments, a compound of the present invention is represented by H and the attendant definitions, wherein X represents O.

In certain embodiments, a compound of the present invention is represented by H and the attendant definitions, wherein Y represents O.

In certain embodiments, a compound of the present invention is represented by H and the attendant definitions, wherein R represents alkyl.

In certain embodiments, a compound of the present invention is represented by H and the attendant definitions, wherein R₄ represents optionally substituted phenyl.

In certain embodiments, a compound of the present invention is represented by H and the attendant definitions, wherein R₅ represents H, alkyl, or aralkyl.

In certain embodiments, a compound of the present invention is represented by H and the attendant definitions, wherein m is 1.

In certain embodiments, a compound of the present invention is represented by H and the attendant definitions, wherein n is 1.

In certain embodiments, a compound of the present invention is represented by H and the attendant definitions, wherein X represents O; and Y represents O.

In certain embodiments, a compound of the present invention is represented by H and the attendant definitions, wherein X represents O; and R represents alkyl.

In certain embodiments, a compound of the present invention is represented by H and the attendant definitions, wherein X represents O; and R₄ represents optionally substituted phenyl.

In certain embodiments, a compound of the present invention is represented by H and the attendant definitions, wherein X represents O; and R₅ represents H, alkyl, or aralkyl.

In certain embodiments, a compound of the present invention is represented by H and the attendant definitions, wherein X represents O; and m is 1.

In certain embodiments, a compound of the present invention is represented by H and the attendant definitions, wherein X represents O; and n is 1.

In certain embodiments, a compound of the present invention is represented by H and the attendant definitions, wherein X represents O; Y represents O; R represents alkyl; and R₄ represents optionally substituted phenyl.

In certain embodiments, a compound of the present invention is represented by H and the attendant definitions, wherein X represents O; Y represents O; R represents alkyl; and R₅ represents H, alkyl, or aralkyl.

In certain embodiments, a compound of the present invention is represented by H and the attendant definitions, wherein X represents O; Y represents O; R represents alkyl; R₄ represents optionally substituted phenyl; and R₅ represents H, alkyl, or aralkyl.

In certain embodiments, a compound of the present invention is represented by H and the attendant definitions, wherein X represents O; Y represents O; R represents methyl; R₄ represents 4-chlorophenyl; R₅ represents ethyl; m is 1; and n is 1.

In certain embodiments, a compound of the present invention is represented by I:

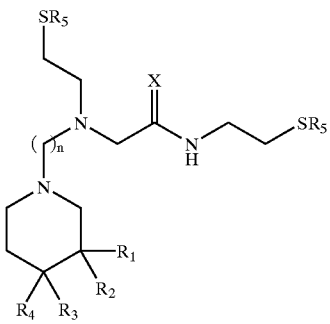

wherein
X represents O or (H)₂;
R represents H, alkyl, alkoxyl, alkylamino, aryl, heteroaryl, aralkyl, heteroaralkyl, acyl, alkoxycarbonyl, or alkylaminocarbonyl;
R₁ represents —C(O)OR;
R₂ represents H;
R₃ represents optionally substituted aryl or heteroaryl;
R₄ represents H;
R₅ represents independently for each occurrence H, alkyl, alkoxyl, alkylamino, aryl, heteroaryl, aralkyl, heteroaralkyl, acyl, alkoxycarbonyl, or alkylaminocarbonyl; and
n is 1, 2, 3, 4, or 5.

In certain embodiments, a compound of the present invention is represented by I and the attendant definitions, wherein X represents O.

In certain embodiments, a compound of the present invention is represented by I and the attendant definitions, wherein R represents alkyl.

In certain embodiments, a compound of the present invention is represented by I and the attendant definitions, wherein R₃ represents optionally substituted phenyl.

In certain embodiments, a compound of the present invention is represented by I and the attendant definitions, wherein R₅ represents H or aralkyl.

In certain embodiments, a compound of the present invention is represented by I and the attendant definitions, wherein n is 3.

In certain embodiments, a compound of the present invention is represented by I and the attendant definitions, wherein X represents O; and R represents alkyl.

In certain embodiments, a compound of the present invention is represented by I and the attendant definitions, wherein X represents O; and R₃ represents optionally substituted phenyl.

In certain embodiments, a compound of the present invention is represented by I and the attendant definitions, wherein X represents O; and R₅ represents independently for each occurrence H or aralkyl.

In certain embodiments, a compound of the present invention is represented by I and the attendant definitions, wherein X represents O; and n is 3.

In certain embodiments, a compound of the present invention is represented by I and the attendant definitions, wherein X represents O; R represents alkyl; and R₃ represents optionally substituted phenyl.

In certain embodiments, a compound of the present invention is represented by I and the attendant definitions, wherein X represents O; R represents alkyl; and R₅ represents independently for each occurrence H or aralkyl.

In certain embodiments, a compound of the present invention is represented by I and the attendant definitions, wherein X represents O; R represents alkyl; R$_3$ represents optionally substituted phenyl; and R$_5$ represents independently for each occurrence H or aralkyl.

In certain embodiments, a compound of the present invention is represented by I and the attendant definitions, wherein X represents O; R represents methyl; R$_3$ represents 4-chlorophenyl; R$_5$ represents independently for each occurrence H or triphenylmethyl; and n is 3.

In certain embodiments, a compound of the present invention is represented by J:

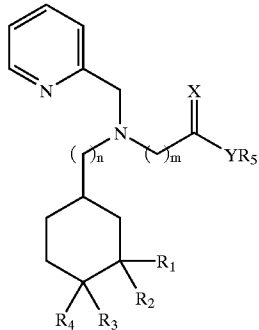

J wherein
X represents O or S;
Y represents O or S;
R represents H, alkyl, alkoxyl, alkylamino, aryl, heteroaryl, aralkyl, heteroaralkyl, acyl, alkoxycarbonyl, or alkylaminocarbonyl;
R$_1$ represents —C(O)OR;
R$_2$ represents H;
R$_3$ represents optionally substituted aryl or heteroaryl;
R$_4$ represents H;
R$_5$ represents H, alkyl, alkoxyl, alkylamino, aryl, heteroaryl, aralkyl, heteroaralkyl, acyl, alkoxycarbonyl, or alkylaminocarbonyl;
m is 1 or 2; and
n is 0, 1, or 2.

In certain embodiments, a compound of the present invention is represented by J and the attendant definitions, wherein X represents O.

In certain embodiments, a compound of the present invention is represented by J and the attendant definitions, wherein Y represents O.

In certain embodiments, a compound of the present invention is represented by J and the attendant definitions, wherein R represents alkyl.

In certain embodiments, a compound of the present invention is represented by J and the attendant definitions, wherein R$_3$ represents optionally substituted phenyl.

In certain embodiments, a compound of the present invention is represented by J and the attendant definitions, wherein R$_5$ represents H, alkyl, or aralkyl.

In certain embodiments, a compound of the present invention is represented by J and the attendant definitions, wherein m is 1.

In certain embodiments, a compound of the present invention is represented by J and the attendant definitions, wherein X represents O; and Y represents O.

In certain embodiments, a compound of the present invention is represented by J and the attendant definitions, wherein X represents O; and R represents alkyl.

In certain embodiments, a compound of the present invention is represented by J and the attendant definitions, wherein X represents O; and R$_3$ represents optionally substituted phenyl.

In certain embodiments, a compound of the present invention is represented by J and the attendant definitions, wherein X represents O; and R$_5$ represents H, alkyl, or aralkyl.

In certain embodiments, a compound of the present invention is represented by J and the attendant definitions, wherein X represents O; and m is 1.

In certain embodiments, a compound of the present invention is represented by J and the attendant, definitions, wherein X represents O; Y represents O; R represents alkyl; and R$_3$ represents optionally substituted phenyl.

In certain embodiments, a compound of the present invention is represented by J and the attendant definitions, wherein X represents O; Y represents O; R represents alkyl; and R$_5$ represents H, alkyl, or aralkyl.

In certain embodiments, a compound of the present invention is represented by J and the attendant definitions, wherein X represents O; Y represents O; R represents alkyl; R$_3$ represents optionally substituted phenyl; and R$_5$ represents H, alkyl, or aralkyl.

In certain embodiments, a compound of the present invention is represented by J and the attendant definitions, wherein X represents O; Y represents O; R represents methyl; R$_3$ represents 4-chlorophenyl; R$_5$ represents ethyl; and m is 1.

In certain embodiments, the present invention relates to a complex comprising a radionuclide and a compound represented by A, B, C, D, E, F, G, H, I, or J. In certain embodiments of this method, the radionuclide is technetium.

In certain embodiments, the present invention relates to methods of imaging brain tissue of a mammal, comprising the step of administering to a mammal a sufficient amount of a complex comprising a radionuclide and a compound represented by A, B, C, D, E, F, G, H, I, or J. In certain embodiments of this method, the radionuclide is technetium.

In certain embodiments, the present invention relates to methods of imaging dopamine transporters in brain tissue of a mammal, comprising the step of administering to a mammal a sufficient amount of a complex comprising a radionuclide and a compound represented by A, B, C, D, E, F, G, H, I, or J. In certain embodiments of this method, the radionuclide is technetium.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydcides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, funarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "Pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compounds of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

Combinatorial Libraries

Combinatorial libraries of the compounds of the present invention may be prepared for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514; the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S.P.A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use protection/deprotection reactions with photolabile protecting groups.

The key points of this technology are illustrated in Gallop et al. (1994) J. Med Chem 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening-strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Synthesis of a Series of Novel Piperidine Monoamine Transporter Ligands

Our proprietary piperidine monoamine transporter ligands, while sharing a structure activity relationships with the related tropanes, are more readily prepared in isomeric and enantiomeric forms allowing us access to a large range of monoamine selectivities. As this selectivity is highly dependant on a number of factors including the orientation of the C-3 ester, as well as the absolute configuration of the ligand, we will prepare both enantiomers of each isomer (Scheme 2) under the conditions utilized in the preliminary studies. The trans-(+) isomer [(+)-10] is readily prepared from the corresponding cis-(−) isomer [(−)-1] by the base catalysed epimerization.[8]

Scheme 2:

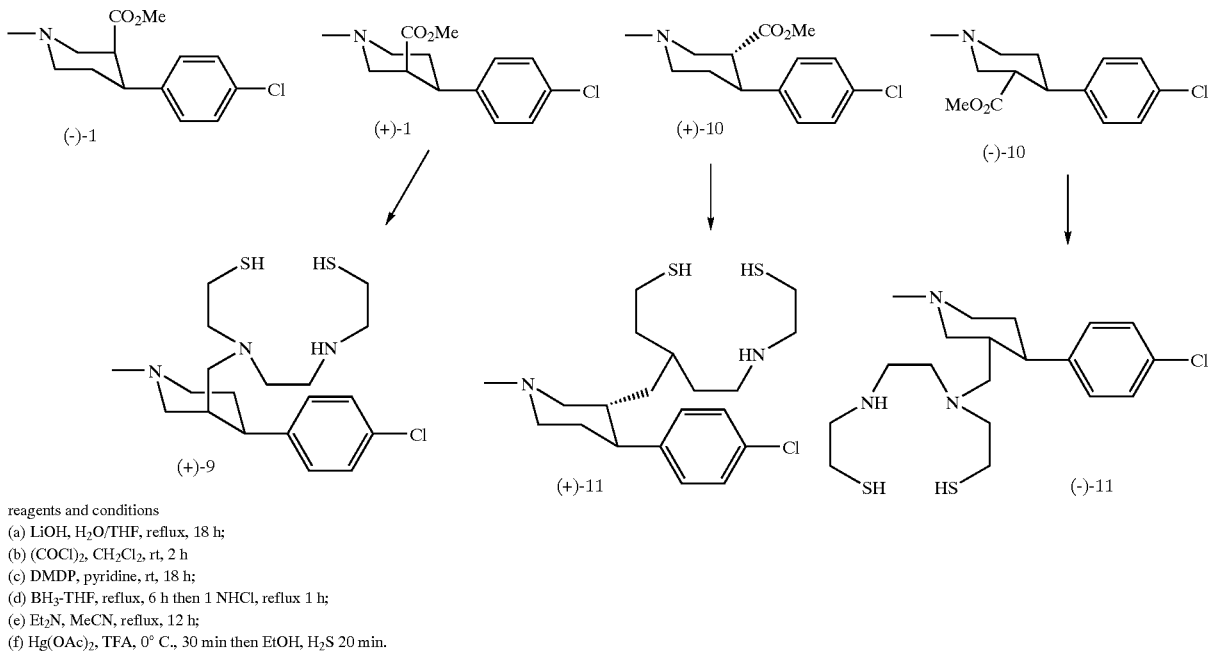

reagents and conditions
(a) LiOH, H$_2$O/THF, reflux, 18 h;
(b) (COCl)$_2$, CH$_2$Cl$_2$, rt, 2 h
(c) DMDP, pyridine, rt, 18 h;
(d) BH$_3$-THF, reflux, 6 h then 1 NHCl, reflux 1 h;
(e) Et$_2$N, MeCN, reflux, 12 h;
(f) Hg(OAc)$_2$, TFA, 0° C., 30 min then EtOH, H$_2$S 20 min.

Based on preliminary studies in which the "3+1" methodology was employed utilizing the N-propylthiol analog of MTPT demonstrated excellent brain uptake, we will prepared a second series of compounds with the N$_2$S$_2$ chelating unit tethered to the nitrogen of the piperidine as shown is Scheme 3. The required N-chloropropyl analogs have been previously prepared in our laboratories and are available in excellent yield. It is anticipated that the relatively unhindered chloride can be directly alkylated with the PMB protected N$_2$S$_2$ chelate group. In the unlikely event that this does not prove to be possible the chelate can be constructed in a stepwise manner similar to that used for our preliminary studies.

Scheme 3:

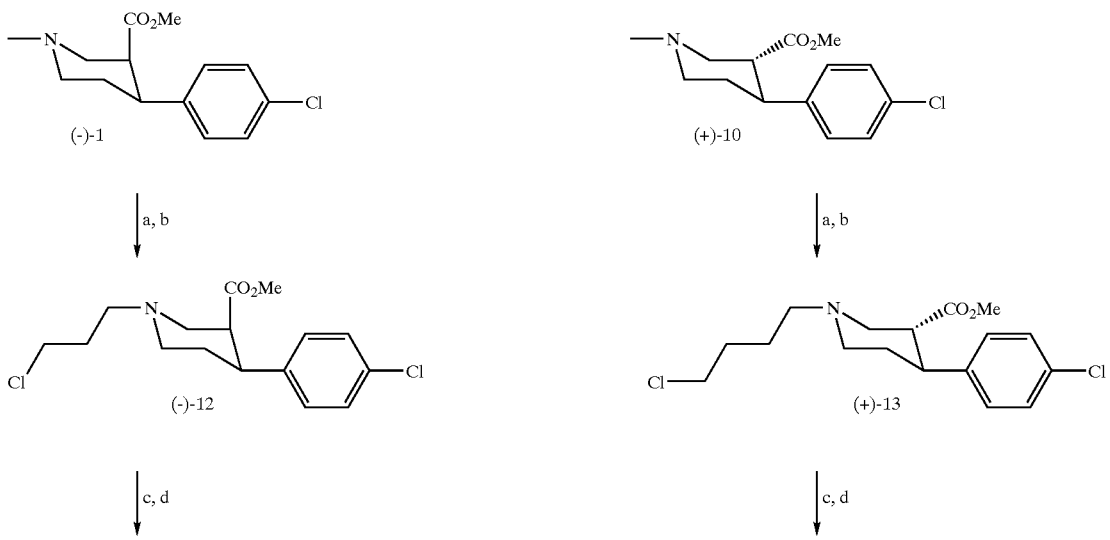

-continued

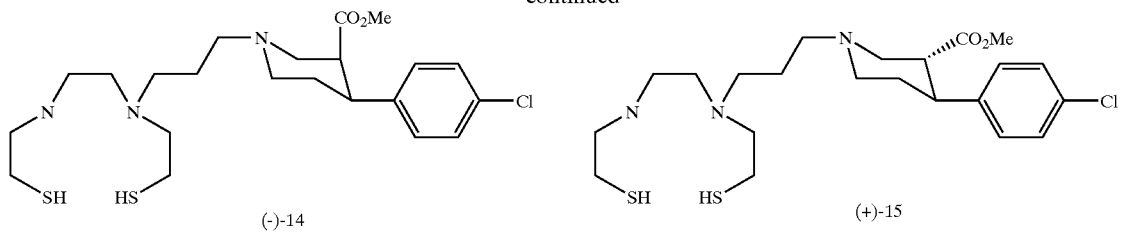

(-)-14    (+)-15 reagents and conditions
(a) ACE-Cl, ClCH$_2$CH$_2$Cl, reflux, 4 h then MeOH, reflux;
(b) BrCH$_2$CH$_2$CH$_2$Cl, K$_2$CO$_3$, acetone, reflux, 12 h
(c) (PMBSCH$_2$CH$_2$NCH$_2$)$_2$, KI, acetonitrile;
(d) Hg(OAc)$_2$, TFA, 0° C., 30 min then EtOH, H$_2$S 20 min.

EXAMPLE 2

Preparation of Rhenium-piperidine Complexes

The properties of the Group VII metals technetium and rhenium are very similar due to their periodic relationship. It is anticipated that the metals will demonstrate similar reaction chemistry, which is often the case for the thiol, nitrogen, phosphine and oxo-chemistry of these two metals. Likewise, perrhenate and pertechnetate have very similar reaction behaviors.[28] The similar reductions of the M(VII) oxo species by SnCl$_2$ allow for easy substitution of the nonradioactive rhenium as a model for the medicinally useful technetium-99m, which routinely uses tin reduced $^{99m}$Tc. Synthesizing the rhenium-piperidine complexes will allow us a facile route to structurally characterize the products. The characterized products can then be used for in vitro pharmacological studies. The periodic relationship between Tc and Re further indicates that Tc-99m radiopharmaceuticals can be designed by modeling analogous rhenium complexes.[29]

The synthesis of the rhenium analogs will follow the established chemistry of the N$_2$S$_2$ system in forming stable, neutral, rhenium-oxo complexes.[30,31] Our N$_2$S$_2$ system, with three easily removed protons forms a predictable metal-complex with an overall net charge of zero. The synthesis of the Re(V) complexes will be accomplished by reacting [TBA][ReOBr$_4$(OPPh$_3$)] with the appropriate piperidine ligand in the ratio of 1:1.2 in 10 mL of methanol and three equivalents of NEt$_3$ as base. The reaction will be allowed to reflux for ½ hour. After cooling the reaction products will be purified using a small column using the method established by Spies and co-workers.[32] Alternatively, the rhenium (V) starting material [ReOCl$_3$(PPh$_3$)$_2$] may be employed as the potential rhenium starting material. This versatile material has proven successful in the past for us in dealing with nitrogen and sulfur donor atoms.[33,34] A schematic depiction of the reaction is illustrated in Scheme 4. The synthesized rhenium-piperidine complexes will be run through a chiral HPLC column for separation and purification purposes following recent procedures.[35] The complexes will then be analyzed by elemental analysis, infrared spectroscopy, mass spectroscopy, and NMR spectroscopy. Finally we will attempt to crystallize the $^{99}$Tc/Re-piperidine complexes.

Scheme 4.
Synthesis of the rhenium-piperidine complexes.

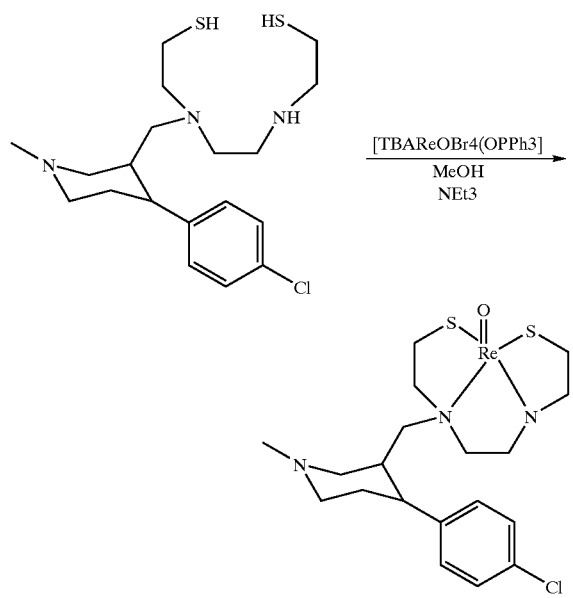

EXAMPLE 3

In vitro Pharmacological Studies on Piperidine Ligands and the Corresponding Rhenium Complexes The pharmacological profile for each of the rhenium-oxo complexes, as well as the free ligands will be determined by the binding affinities at each of the monoamine transporters. The binding affinity at DAT (human recombinat, expressed in CHO cells) will be determined by its ability to displace 0.15 nM [$^{125}$I]RTI-55.[36] The binding affinity at NET (human recombinat, expressed in MDCK) will also be determined by the ability of the complexes to displace 0.20 nM [$^{125}$I]RTI-55.[37] The binding affinity at 5-HTT (human recombinat, expressed in HEK-293) will be determined by its ability to displace 0.15 nM [$^{125}$I]RTI-55.[36] All compounds will initially be tested at 10$^{-6}$ M (in duplicate) and compounds that exhibit displacement of >40% will be assayed (at 10$^{-7}$, 10$^{-8}$, 10$^{-9}$ M in duplicate) and approximate IC$_{50}$ values are calculated.

EXAMPLE 4

Preparation and Characterization of 99mTc Labeled Versions of High Affinity Piperidines Preparation of the Tc-99m-labeled piperidine complexes will be achieved by adding 10 mCi of $TcO_4^-$ to a 0.9% saline solution of sodium gluceptate (200 mg/3 ml). After 20 minute incubation, 400 ul will be added to a solution of 400 ul of sodium acetate (50 mM, pH 5.2) and the appropriate piperidine ligand (50 ug). The mixture will be heated at 80° C. for 30 min. The mixture is then extracted with ethyl acetate (3×1 mL), dried over sodium sulfate, and dried under $N_2$. The residue is then re-dissolved in ethanol (400 ul) and purity checked via HPLC by a Hamilton PRP-1 (5 mm, 25 cm) column using $CH_3CN$ buffer to elute the reaction products. The buffer consists of dimethylglutaric acid (0.05 mM) which is then pH adjusted to 7.0 with NaOH.

As part of our preliminary studies we have already developed the proposed stability tests for $^{99m}$Tc-labeled piperidine complexes. The stability of the radiolabeled compounds in solution and in plasma will be determined as a function of time and solution conditions such as pH and solvents. Specifically, after radiolabeling and isolation, the product will be allowed to sit at room temperature for 48 hours after which HPLC analysis will be performed to check for degree of label retention, as well as potential product degradation. We will analyze for the reformation of $TcO_4^-$ and the presence of the reduced species $TcO_2$. To assist in predicting the in-vivo label stability ligand challenges will be performed. Specifically, the product will be incubated with a competing biological ligand such as cysteine, albumin, and transferrin, testing the stability of the radiolabel via HPLC analysis. Finally we will test the product in plasma as a function of time and pH.

EXAMPLE 5

In vivo Rat Studies of Brain Uptake of Certain $^{99m}$Tc-complexes

Once pharmacological studies are complete, demonstrating the binding affinity of the ligands and rhenium complexes for the dopamine transporter, and the Tc-99m labeling methods are elucidated, preliminary rat studies will be performed. The studies will evaluate uptake and retention in the brain. The evaluations will be performed by tissue sampling at various times following administration of the Tc-99m-piperidine complexes to the rats. The studies will be repeated with β-CIT pretreatment, which competes with dopamine transporter binding, to determine if specific uptake can be blocked. A comparison of brain uptake and retention within the series, as well as with other SPECT DAT complexes, will be performed.

EXAMPLE 6

Synthesis of (+)-4β-(4'-Chlorophenyl)-1-methylpiperidine-3β-[2-(4'-methoxybenzylthio)ethyl)aminomethyl]-N-[2-(4'-methoxybenzylthio)ethyl)]acetaminde ((+)-5)

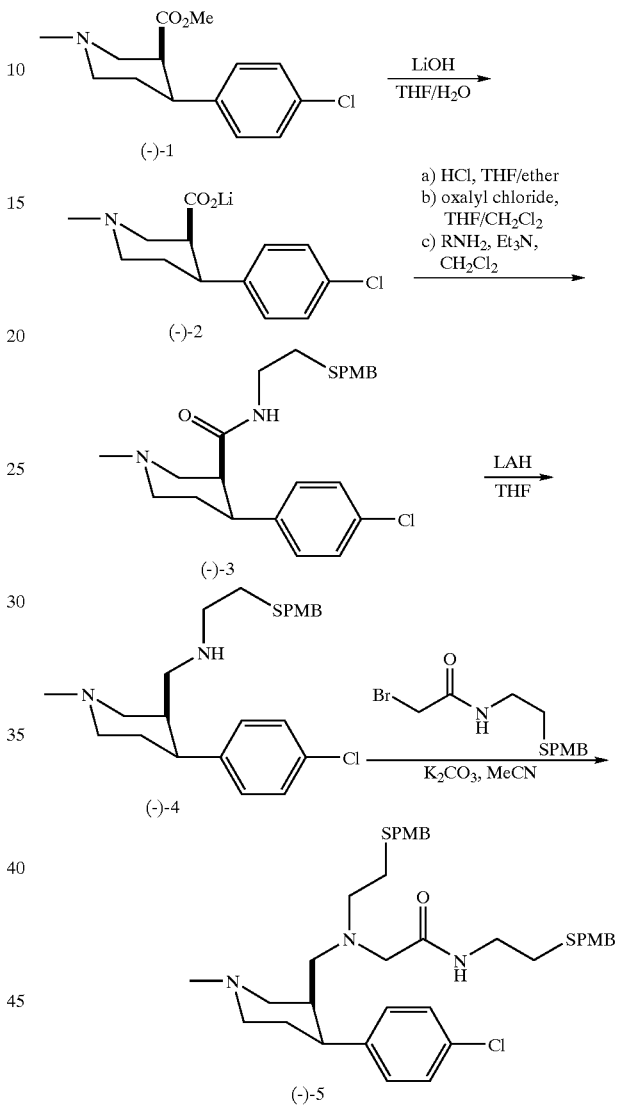

(−) Lithium 4β-(4'-Chlorophenyl)-1-methylpiperidine-3β-carboxylate, (−)-2

A mixture of (−)-1 (Kozikowski et. al. *J. Med. Chem.* 1998, 41, 1962–1969, 5.0 g, 19 mmol) and LiOH (670 mg, 28 mmol) in THF/$H_2O$ (2:1, 150 mL) was heated to refulx for 16 h. The resulting clear colorless solitio was then concentrated to 30 mL and washed with ether (100 mL). The aqueous solution was then concentrated to afford (−)-2 as a white solid (7.28 g, quantitative) that was used as obtained.

(+) Lithium 4β-(4'-Chlorophenyl)-1-methylpiperidine-3β-carboxylate, (+)-2

Prepared as described above from (+)-1 to afford (+)-2 as a white solid (quantitative) that was used as obtained.

(−)-N-[2-(4'-methoxybenzylthio)ethyl] 4β-(4'-Chlorophenyl)-1-methylpiperidine-3β-carboxyamide, (−)-3

To a suspension of (−)-2 (3.50 g 8.9 mmol) in THF (50 mL) was added a 2 M solution of HCl in anhydrous ether (25 mL). The resulting mixture was stirred for 30 min at rt and concentrated. The residue obtained was suspended in THF/CH$_2$Cl$_2$ (1:1, 50 mL) and oxalyl chloride (4.0 mL, 48 mmol) was added dropwise. The resulting suspension was stirred at rt for 2 h and the resulting yellow solution was concentrated to afford the crude acid chloride as a yellow foam. This foam was disolved in THF (100 mL) and treated with a mixture of 1-amino-2-(4'methoxybenzylthio)ethane (3.8 g, 19 mmol) and Et$_3$N (5.4 mL, 39 mmol). The resulting reaction was stirred at rt for 2 h and then concentrated. The residue obtained was suspended in saturated NaHCO$_3$ (75 mL) and extracted with CH$_2$Cl$_2$ (2×75 mL). Flash chromatography (EtOAc/Et$_3$N, 9:1, SiO$_2$) afforded (−)-3 (2.44 g, 63% from (−)-1) as a celar colorless oil: R$_f$ 0.6 (EtOAc/Et$_3$N, 9:1); [α]$_D$−71.0 (c 1.33, CHCl$_3$); $^1$H NMR (CDCl$_3$) δ1.69–1.74 (m, 1H), 2.06–2.18 (m, 1H), 2.23–2.36 (m, 4H), 2.56 (t, 2H, J=6.2 Hz), 2.69 (m, 1H), 2.79 (dt, 1H, J=4.7, 11.0 Hz), 3.02–3.08 (m, 2H), 3.23–3.29 (m, 1H), 3.43–3.51 (m, 1H), 3.69 (s, 3H), 3.80 (s, 3H), 6.85 (d, 2H, J=8.6 Hz), 7.07 (d, 2H, J=9.5 Hz), 7.20 (d, 2H, J=9.5 Hz), 7.23 (d, 2H, J=8.6 Hz), 8.99 (m, 1H)].

(+)-N-[2-(4'-methoxybenzylthio)ethyl] 4β-(4'-Chlorophenyl)-1-methylpiperidine-3β-carboxyamide, (+)-3

Prepared as described above from (+)-2 to afford (+)-3 (8.6 g, 88% from (+)-1) as a clear colorless oil: [α]$_D$+70.4 (c 2.09, CHCl$_3$).

(−)-4β-(4'-Chlorophenyl)-1-methylpiperidine-3β-[2-(4'-methoxybenzylthio)ethyl)aminomethyl], (−)-4

Lithium aluminum hydride (430 mg, 11 mmol) was added portionwise to a solution of (−)-3 (2.4 g, 5.6 mmol) in THF (50 mL). The resulting suspension was heated to reflux for 18 h and then carefully quenched with 1 N aqueous NaOH (10 mL). The resulting mixture was stirred for 30 min and then filtered through celite. The aqueous layer was separated from the filtrates and extracted with CH$_2$Cl$_2$ (2×25 mL). The pooled organic extracts were dried (Na$_2$SO$_4$) and concentrated. Flash chromatography (EtOAc/Et$_3$N, 9:1, SiO$_2$) afforded (−)-4 (1.3 g, 55%) as a clear viscous oil: R$_f$ 0.3 (EtOAc/Et$_3$N, 9:1); [α]$_D$−45.9 (c 1.50, CHCl$_3$); $^1$H NMR (CDCl$_3$) δ1.69–1.77 (m, 1H), 2.02–2.11 (m, 3H), 2.18–2.28 (m, 2H), 2.30 (s, 3H), 2.45–2.49 (m, 2H), 2.55–2.62 (m, 2H), 2.78–2.85 (m, 2H), 3.01–3.05 (m, 1H), 3.03 (d, 1H, J=7.4 Hz), 3.59 2H), 3.78 (s, 3H), 6.81 (d, 2H, J=8.6 Hz), 7.14 (d, 2H, J=8.2 Hz), 7.16 (d, 2H, J=8.6 Hz), 7.27 (d, 2H, J=8.2 Hz).

(+)-4β-(4'-Chlorophenyl)-1-methylpiperidine-3β-[2-(4'-methoxybenzylthio)ethyl)aminomethyl], (+)-4

Prepared as described above from (+)-3 to afford (+)-4 (2.46 g, 46%) as a clear colorless oil [α]$_D$45.1 (c 1.74, CHCl$_3$).

(+)-4β-(4'-Chlorophenyl)-1-methylpiperidine-3β-[2-(4'-methoxybenzylthio)ethyl)aminomethyl] N-[2-(4'-methoxybenzylthio)ethyl)]acetaminde (+)-5

A mixture of (+)-4 (1.45 g, 3.5 mmol), N-[2-(4'-methoxybenzylthio)ethyl)] 2-bromoacetaminde (2.0 g, 6.9 mmol) and K$_2$CO$_3$ (1.4 g, 10 mmol) was stirred at rt in MeCN (10 mL). After 28 h the solvents were removed and the residue suspended in saturated NaHCO$_3$ (50 mL) and extracted with CH$_2$Cl$_2$ (3×25 mL). The pooled organic extracts were dried (Na$_2$SO$_4$) and concentrated. Flash chromatography (EtOAc/Et$_3$N, 9:1, SiO$_2$) afforded (+)-5 (871 mg, 38%) as a clear viscous oil: R$_f$ 0.5 (EtOAc/Et$_3$N, 9:1); [α]$_D$+66.1 (c 1.40, CHCl$_3$); $^1$H NMR (CDCl$_3$) δ1.61–1.66 (m, 1H), 1.72–1.79 (m, 1H), 1.89–2.03 (m, 3H), 2.04 (s, 2H), 2.23 (s 3H), 2.27–2.47 (m, 4H), 2.53 (t, 2H, J=7.0 Hz), 2.66–2.83 (m, 2H), 2.86–2.95 (m, 2H), 3.13 (d, 1H, J=8.9 Hz), 3.32–3.46 (m, 2H), 3.57 (s, 2H), 3.68 (s, 2H), 3.77 (s, 3H), 3.78 (s, 3H), 6.80–6.87 (m, 4H), 7.04 (d, 2H, J=8.2 Hz), 7.16 (d, 2H, J=8.2 Hz), 7.23–7.27 (m, 4H), 8.10 (m, 1H).

EXAMPLE 7

Synthesis of (−)-N4β-(4'-Chlorophenyl)-1-methylpiperidine-3β-methyl N-(2-Pyridyl)methylamine ((−)-7)

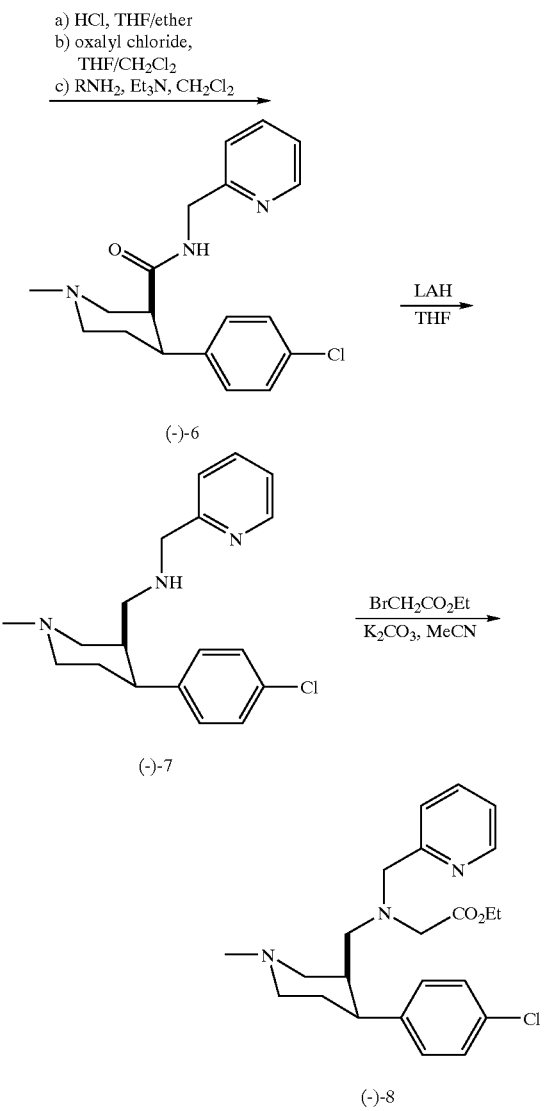

(−)-N-(2-Pyridyl)methyl 4β-(4'-Chlorophenyl)-1-methylpiperidine-3β-carboxyamide, (−)6: To a suspension of (−)-2

(3.7 g, 9.7 mmol) in THF (50 mL) was added a 2 M solution of HCl in anhydrous ether (25 mL). The resulting mixture was stirred for 30 min at rt and concentrated. The residue obtained was suspended in THF/CH$_2$Cl$_2$ (1:1, 50 mL) and oxalyl chloride (4.5 mL, 52 mmol) was added dropwise. The resulting suspension was stirred at rt for 2 h and the resulting yellow solution was concentrated to afford the crude acid chloride as a yellow foam. This foam was disolved in THF (100 mL) and treated with a mixture of 2-aminomethylpyrdine (1.8 mL, 18 mmol) and Et$_3$N (5.4 mL, 39 mmol). The resulting reaction was stirred at rt for 2 h and then concentrated. The residue obtained was suspended in saturated NaHCO$_3$ (75 mL) and extracted with CH$_2$Cl$_2$ (3×75 mL). Flash chromatography (EtOAc/Et$_3$N, 9:1, SiO$_2$) afforded (−)-6 (1.82 g, 55% from (−)-1) as a yellow colorless oil: R$_f$ 0.33 (EtOAc/Et$_3$N, 9:1); [α]$_D$−60.9 (c 1.21, CHCl$_3$); $^1$H NMR (CDCl$_3$) δ1.68 (dd, 1H, J=2.4, 13.3 Hz), 2.05–2.12 (m, 1H), 2.26–2.37 (m, 5H), 2.74 (m, 1H), 2.77–2.80 (m, 1H), 3.04–3.13 (m, 2H), 4.50 (abq, 2H), 6.97 (d, 2H, J=8.5 Hz), 7.14 (d, 2H, J=8.5 Hz), 7.19 (dd, 1H, J=5.0, 7.0 Hz), 7.26 s, 1H), 7.64 (m, 1H), 8.57 (d, 1H, J=4.3 Hz), 9.45 (m, 1H)].

(+)-N-(2-Pyridyl)methyl 4β-(4'-Chlorophenyl)-1-methylpiperidine-3β-carboxyamide, (+)-6

Prepared as described above from (+)-2 to afford (+)-6 (4.6 g, 68% from (+)-1) as a yellow colorless oil: [α]$_D$+60.4 (c 1.03, CHCl$_3$).

(−)-N-4β-(4'-Chlorophenyl)-1-methylpiperidine-3β-methyl N-(2-Pyridyl)methylamine, (−)-7

Lithium aluminum hydride (400 mg, 11 mmol) was added portionwise to a solution of (−)-6 (1.8 g, 5.3 mmol) in THF (50 mL). The resulting suspension was heated to reflux for 18 h and then carefully quenched with 1 N aqueous NaOH (10 mL). The resulting mixture was stirred for 30 min and then filtered through celite. The aqueous layer was separated from the filtrates and extracted with CH$_2$Cl$_2$ (3×25 mL). The pooled organic extracts were dried (Na$_2$SO$_4$) and concentrated. Flash chromatography (CH$_2$Cl$_2$/EtOH/Et$_3$N, 7:2:1, SiO$_2$) afforded (−)-7 (352 mg, 20%) as a dark viscous oil: R$_f$ 0.65 (EtOAc/Et$_3$N, 9:1); [α]$_D$−39.4 (c 1.41, CHCl$_3$)

(+)-N-4β-(4'-Chlorophenyl)-1-methylpiperidine-3β-methyl N-(2-Pyridyl)methylamine, (+)-7

Prepared as described above from (+)-6 to afford (+)-7 (2.46 g, 46%) as a clear colorless oil: [α]$_D$+45.1 (c 1.74, CHCl$_3$).

EXAMPLE 8

Synthesis of a Radiolabeled Piperidine Complex ((+)-14)

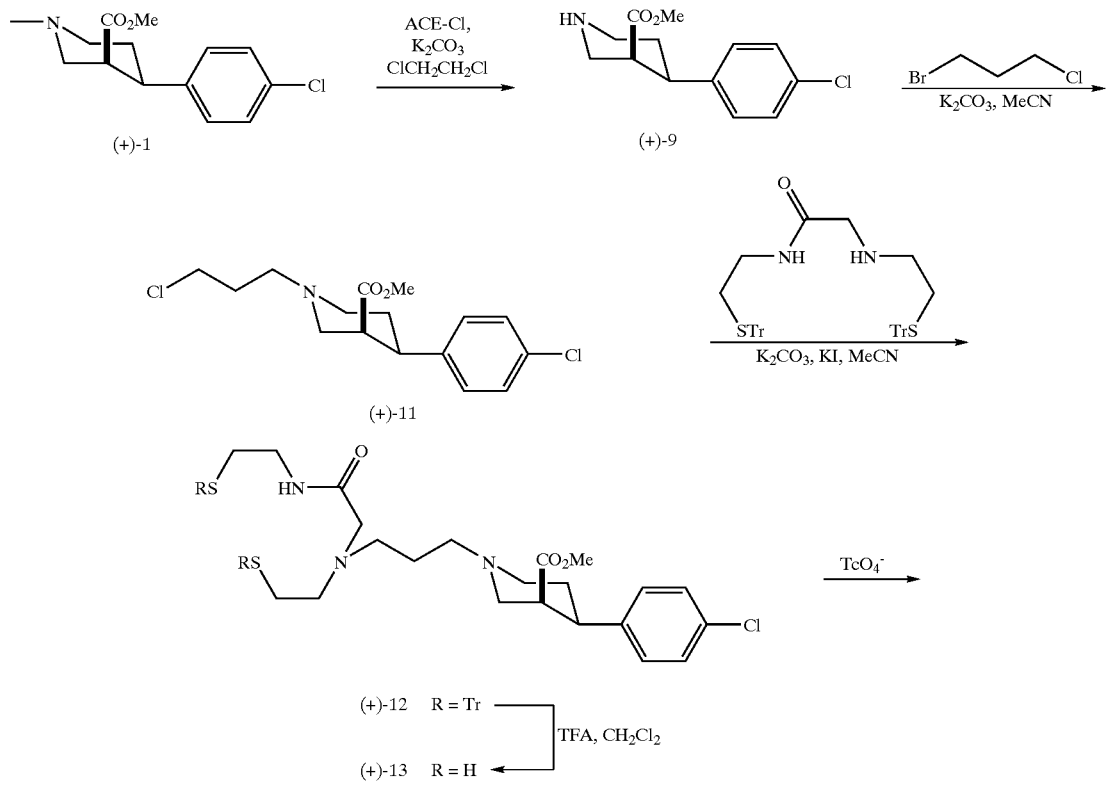

-continued

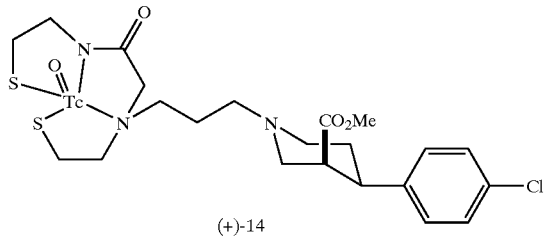

(+)-14

(−)-Methyl 4β-(4-Chlorophenyl)piperidine-3β-carboxylate (−)-9

A solution of (−)-1 (8.9 g, 33 mmol), 1-chloroethyl chloroformate (5.4 mL, 50 mmol), and $K_2CO_3$ (150 mg) in 1,2-dichloroethane (100 mL) was heated to reflux for 2 h and diluted with a 1 M solution of HCl in ether (40 mL). the resulting mixture was filtered through a pad of $SiO_2$ and the pad was washed with $CH_2Cl_2$ (100 mL). The combined filtrates were concentrated, diluted with MeOH (100 mL), and heated to reflux for 16 h. After 16 h the solvents were removed and the residual oil was suspended in 10% HCl (150 mL), washed with EtOAc (100 mL), made basic with $NH_4OH$ and extracted with $CH_2Cl_2$ (3×150 mL). The pooled $CH_2Cl_2$ layers were concentrated and subjected to chromatography (EtOAc/$Et_3N$, 9:1) to afford (−)-9 (6.8 g, 78%) as a clear colorless oil: $R_f$=0.15 (EtOAc/$Et_3N$, 9:1); $[\alpha]_D$−177 (c 0.92, EtOH); $^1H$ NMR ($CDCl_3$) δ1.76 (dd, 1H, J=2.4, 13.2 Hz), 2.04 (br s, 1H), 2.46 (ddd, 1H, J=4.4, 12.7, 18.0 Hz), 2.80–2.89 (m, 2H), 3.07–3.13 (m, 2H), 3.40–3.50 (m, 2H), 3.56 (s, 3H), 7.24 (d, 2H, J=8.3 Hz), 7.38 (d, 2H, J=8.3 Hz); $^{13}C$ NMR ($CDCl_3$) δ26.7, 42.9, 45.7, 46.6, 49.1, 51.0, 128.3, 128.5, 132.1, 141.9, 173.8; MS m/z (%) 253 (19), 194 (37), 115 (48), 57 (100).

(+)-Methyl 4β-(4-Chlorophenyl)piperidine-3β-carboxylate (+)-9

Prepared as described above from (+)-1 to afford (+)-9 (78%) as a clear viscous oil: $[\alpha]_D$+190 (c 1.1, EtOH).

(+)-Methyl 4β-(4-Chlorophenyl)-1-(3-chloropropyl)piperidine-3β-carboxylate (+)-11

A solution of (+)-9 (1.4 g, 5.5 mmol), bromochloropropane (1.5 mL, 15 mmol), and $K_2CO_3$ (4.1 g, 30 mmol) in acetone (100 mL) was stirred at rt for 18 h. The reaction mixture was diluted with saturated $NaHCO_3$ (100 mL) and extracted with ether (2×75 mL). The pooled organic extracts were washed with water (50 mL), brine (50 mL) and dried ($Na_2SO_4$). Chromatography (hexanes/EtOAc, 1:1, $SiO_2$) afforded (+)-11 (1.5 g, 83%) as a clear colorless oil: $R_f$=0.8 (hexanes/EtOAc, 1:1); $[\alpha]_D$+26.6 (c 1.05, $CHCl_3$); $^1H$ NMR ($CDCl_3$) δ1.36 (m, 1H), 1.77 (m, 1H), 1.99–2.18 (M, 3H), 2.27–2.42 (m, 3H), 2.52–2.62 (m, 3H), 3.35 (m, 1H), 3.08–3.19 (m, 5H), 6.96 (d, 2H, J=8.7 Hz), 7.14 (d, 2H, J=8.7 Hz). MS m/z (%) 331 (3), 329 (9), 294 (12), 266 (100), 223 (27).

(+)-Methyl 4β-(4-Chlorophenyl)-1-(3-[N-(trytylthio)ethyl]acetamidyl]-N-(trytylthio)ethylaminopropyl)piperidine-3β-carboxylate (+)-12

A solution of (+)-11 (260 mg, 0.79 mmol), N-(trytylthio) ethyl]acetamidyl N-trytylthio)ethylamine (535 mg, 0.79 mmol), KI (10 mg) and $K_2CO_3$ (140 mg, 1 mmol) in MeCN (25 mL) was heated to reflux for 8 h. The solvents were removed and the residue was suspended in ½ saturated $NaHCO_3$ (50 mL) and extracted with ether (3×25 mL). The pooled organic extracts were dried ($Na_2SO_4$) and concentrated. Chromatography (hexanes/EtOAc, gradient, $SiO_2$) afforded (+)-12 (110 mg, 14%) as a clear colorless oil: $R_f$=0.4 (EtOAc).

(+)-Methyl 4β-(4-Chlorophenyl)-1(3-[N-trytylthio)ethyl]acetamidyl]-N-(trytylthio)ethylaminopropyl)piperidine-3β-carboxylate (+)-13

To a solution of (+)-12 (10 mg) in $CH_2Cl_2$ (250 μL) was added TFA (300 μL) and triethylsilane (200 μL). The solution was allowed to stir at rt for 30 minutes. The solvents were removed under a stream of $N_2$ and washed with hexanes (3×1 mL). The residue of (+)-13 (6 mg, 80%) obtained was disolved in DMSO (600 μL).

Radiolabeling of (+)-13 with Tc-99m

[$^{99m}$Tc]pertechnetate (10 mCi) was added to a 0.9% saline solution of Na gluceptate (200 mg/3 mL). After 20 minutes, an alquot (400 μL) was added to a solution of NaOAc (400 μL, 50 mM, pH 5.2) and (+)-13 (1 mg=100 μl DMSO). The mixture was incubated at room temperature for 30 minutes whereupon it was analyzed via HPLC for product yield and purity. The HPLC was a Varian ProStar 345 equipped with a Vydac C18 column. The Tc-99m-labeled piperidine complex was eluted using a gradient (0–100% B) method with the solvents $H_2O$+0.1% TFA and $CH_3CN$+0.1% TFA. After HPLC separation, the TFA was removed using a Waters C18 Sep-Pak and filtered through a Millipore Millex-GV 0.22 μm filter. The final product was diluted and made isotonic by addition of 0.9% saline to afford a dose (10 mL) containing 3.98 mCi of activity. HPLC analysis was performed on the dose at 3 and 24 h after preparation, the product was >90% pure at both time points.

REFERENCES CITED IN THE SPECIFICATION

1. Ilgin, N., Zubieta, J., Reich, S. G., Dannals, R. F., Frost J. J. Positron Emnission Tomographic Imaging of the Dopamine Transporter in progressive supranuclear palsy and Parkinson's disease. Neurology (1999):52(6):1221–6.
2. Hantraye P, Brownell A-L, Elmaleh D R, Spealman R D, Wullner U, Brownell G L, Madras B K, Isacson O. Dopamine fiber detection by $^{11}$C-CFT and PET in a primate model of Parkinsonism. NeuroReport (1992) 3:265–268.
3. Stoof J C, Winogrodzka A, van Muiswinkel F L, Wolters E C, Voom P, Groenewegen H J, Booij J, Drukarch B. Leads for the development of neuroprotective treatment in Parkinson's disease and brain imaging methods for estimating treatment efficacy. Eur J Pharmacol (1999) 375 (1-3):75–86.
4. Innis R, Baldwin R, Sybirska E, Zea Y, Laruelle M, al-Tilriti M, Charney D, Zoghbi S, Smith E, Wisniewski G, et al. Single photon emission computed tomography imaging of monoamine reuptake sites in primate brain with [$^{123}$I]CIT. *Eur J Pharmacol* (1991) 200(2-3):369–370.

5. Shaya E K, Scheffel U, Dannals R F, Ricaurte G A, Carroll F I, Wagner H N Jr, Kuhar M J, Wong D F. In vivo imaging of dopamine reuptake sites in the primate brain using single photon emission computed tomography (SPECT) and iodine-123 labeled RTI-55. *Synapse* (1992) 10(2):169–172.

6. Neumeyer J L, Wang S Y, Milius R A, Baldwin R M, Zea-Ponce Y, Hoffer P B, Sybirska E, al-Tikriti M, Charney D S, Malison R T, et al. [$^{123}$I]-2 beta-carbomethoxy-3 beta-(4-iodophenyl)tropane: high-affinity SPECT radiotracer of monoamine reuptake sites in brain. *J Med Chem* (1991) 34(10):3144–146.

7. Kung, H. F., Kim, H-J., Kung, M-P., Meegalla, S. K., Plossl, K., Lee, H-K. Imaging of dopamine transporters in humans with technetium-99m TRODAT-1. *Eur. J. Nuc. Med.* (1996) 11: 1527–1530.

8. Meegalia, S. K, Plossl, K, Kung, M.-P., Chumpradit, S., Stevenson, A. D., Kushner, S. A., McElgin, W. T., Mozley, D. P., Kung, H. F. Synthesis and characterization of technetium-99m-labeled tropanes as dopamine transporter-imaging agents. *J. Med. Chem.* (1997) 40: 9–17.

9. Zhuang, Z-P., Mu, M., Kung, M-P., Plossi, K., Kung, H. F. Homologue of [99mTc] TRODAT-1 as dopamine transporter imaging agent. *J. Labeled. Cpd. Radiopharm.* (1999) 42:S351.(abstract)

10. Smith, M. P., Johnson, K. M., Zhang, M., Flippen-Anderson, J. L., Kozikowski, A. P. Tuning the selectivity of monoamine transporter inhibitors by the stereochemistry of the nitrogen lone pair. *J. Amer. Chem. Soc.* (1998) 120: 9072–9073.

11. Hamilton, G. S., Steiner, J. P. Immunophilins: beyond immunosuppression. *J. Med. Chem.* (1998)41: 5119–5143.

12. Villemagne, V. L., Rothman, R. B., Yokoi, F., Rice, K. C., Matecka, D., Dannals, R. F., Wong, D. F. Doses of GBR12909 that suppress cocaine self-administration in non-human primates substantially occupy dopamine transporters as measured by [11C] WIN35,428 PET scans. *Synapse* (1999) 32(1):44–50.

13. Cook, E. H., Krasowski, M. D., Cox, N. J., Olkon, D. M., Kieffer, J. E., Leventhal, B. L. Association of attention-deficit disorder and the dopamine transporter gene. *Am. J. Hum. Genet.* (1995) 56(4): 993–998.

14. Carroll F I, Lewin A H, Boja J W, Kuhar M J. Cocaine receptor: biochemical characterization and structure-activity relationships of cocaine analogues at the dopamine transporter. *J Med Chem* (1992) 35(6):969–981.

15. Fowler J S, Volkow N D, Wolf A P, Dewey S L, Schlyer D J, Macgregor R R, Hitzemann R, Logan J, Bendriem B, Gatley S J, et al. Mapping cocaine binding sites in human and baboon brain in vivo. *Synapse* (1989) 4(4):371–377.

16. Frost, J. J., Rosier, A. J., Reich, S. G., Smith, J. S., Ehlers, M. D., Snyder, S. H., Ravert, H. T., Dannals, R. F., Positron Emission tomographic imaging of the dopamine transporter with [$^{11}$C]-WIN 35,428 reveals marked declines in mild Parkinson's' disease. *Ann. Neurol.* (1993) 34: 423–431.

17. Yung, B. C. K., Dannals, R. F., Kuhar, M. J., Shaya, E. K., Ravert, H. T., Chen, C., Chan, B., Scheffel, U., Ricaurte, G., Folio, T., Wagner, H. N., Neumeyer, M., Wong, D. F. In vivo dopamine transporter sites imaging in human using [$^{11}$C]-WIN35,428 positron emission tomography (PCET) [abstract]. *J. Nucl. Med.* (1993) 34: 197.

18. Innis, R. B., Seibyl, J. P., Scanley, B. E., et. al. Single photon emission computed tomographic imaging demonstrates loss of striatal dopamine transporters in Parkinson's disease. *Proc. Natl. Acad. Sci. USA* (1993) 90: 11965–11969.

19. Mozley, P. D., Stubbs, J. B., Kim, H. J., McElgin, W. T., Kung, M. P., Meegalla, S. K., Kung, H. F. Dosimetry of an iodine-123-labeled tropane to image dopamine transporters. *J. Nucl. Med.* (1996) 37:151–159.

20. Meegalla, S., Plossl, K., Kung, M-P., Stevenson, D. A., Liable-Sands, L. M., Rheingold, A. L., Kung, H. F. First example of a 99mTc complex as a dopamine transporter Imaging agent. *J. Am. Chem. Soc.* (1995) 117: 11037–11038.

21. Kaufman M J, Madras B K. Distribution of cocaine recognition sites in monkey brain. *Synapse* 1992;12:99–111.

22. Meltzer P C, Liang A, Brownell A-L, Elmaleh D R, Madras B K. Substituted 3-phenyltropane analogs of cocaine: synthesis, inhibition of binding at cocaine recognition sites, and Positron Emission Tomography Imaging. *J. Med. Chem.* (1993) 36,:855–862.

23. Reedijk J., Medicinal Applications of heavy-metal compounds. *Curr. Opin. Chem. Biol.* (1999)3(2): 236–240.

24. Hom, R. K., Katzenellenbogen, J. A. Technetium-99m-labeled receptor-specific small-molecule radiopharmaceuticals: recent developments and encouraging results. *Nuc. Med. and Biol.* (1997) 24: 485–498.

25. Hoepping, A., Babich, J., Zubieta, J. A., Johnson, K. M., Machill, S., Kozikowski, A. P. Synthesis and biological evaluation of two novel DAT-binding technetium complexes containing a piperidine based analogue of cocaine. *Bioorg. Med. Chem. Lett.* (1999) 9: 3211–3216.

26. Warren G L, Caldwell J H, Kremer P A, et al: New iodinated phenyl fatty acids for imaging myocardial metabolism. *J. Nucl. Med.* (1986) 27: 939–940 (abstr.).

28. Rose, D. J., Maresca, K. P., Nicholson, T., Davison, A., Jones, A. G., Babich, J., Fischman, A., Graham, W., DeBord, J. R. D., Zubieta, J. Synthesis and Characterization of Organohydrazine Complexes of Technetium, Rhenium, and Molybdenum with the {M(η1-HxNNR)(η2-HyNNR)} Core and Their Relationship to Radiolabeled Organohydrazine-Derivatized Chemotactic Peptides with Diagnostic Applications. *Inorg. Chem.* (1998) 37: 2701–2716.

29. Nicholson, T., Cook, J., Davison, A., Rose, D. J., Maresca K. P., Zubieta, J. A., Jones, A. G. The synthesis and characterization of [MCl$_3$(N=NC$_5$H$_4$NH)(HN=NC$_5$H$_4$N)] from [MO$_4$]$^-$ (where M=Re, Tc) organodiazenido, organodiazene-chelate complexes. *Inorg. Chim. Acta* (1996) 252: 421–426.

30. Kung, H. F., Yu, C. C., Billings J., Molnar, M., Blau, M. Synthesis of New Bis(aminoethanethiol) (BAT) derivatives: Possible ligands for 99mTc brain imaging agents. *J. Med. Chem.* (1985) 28: 1280–1284.

31. Chiotellis, E., Varvarigou, A. D., Maina, T H., Stassinopoulou, C. I. Comparative evaluation of 99mTc-labeled aminothiols as possible brain perfusion imaging agents. *Nucl. Med. Biol.* (1988) 15: 215–223.

32. Spies, H., Fietz, T., Pietzsch H-J., Johannsen, B., Leibnitz, P., Reck, G., Scheller, D., Klostermann, K. Neutral oxorhenium(V) complexes with tridentate dithiolates and monodentate alkane- or arene-thiolate coligands. *J. Chem. Soc. Dalton Trans.* (1995) 2277–2280.

33. Maresca, K. P., Bonavia, G. H., Babich, J. W., Zubieta, J. A. Expansion of the '3+1' concept of oxorhenium-thiolate chemistry to cationic and binuclear complexes. *Inorg. Chem. Comm.* (1998)1: 209–212.

34. Rose, D. J., Maresca, K. P., Kettler, P. B., Chang, Y. D., Soghomonian, V., Chen, Q., Abrams, M. J., Larsen, S. K., Zubieta, J. Synthesis and characterization of rhenium thiolate complexes. *Inorganic Chemistry* (1995) 35: 3556–3562.
35. Luyt, L. G., Jenkins, H. A., Hunter, D., H. An N2S2 bifunctional chelator for technetium-99m and rhenium: Complexation, conjugation, and epimerization to a single isomer. *Bioconjugate Chem.* (1999) 10: 470–479.
36. Gu, H.; Wall, S. C.; Rudnick, G. Stable expression of biogenic amine transporters reveals differences in inhibitor sensitivity, kinetics, and ion dependence. *J. Biol. Chem.* (1994) 269, 7124–7130
37. Galli, A.; DeFelice, L. J.; Duke, B. J.; Moore, K. R.; Blakely, R. D. Sodium-dependent norepinephrine-induced currents in norepinephrine-transporter-transfected HEK-293 cells blocked by cocaine and antidepressants. *J. Exp. Biol.* (1995) 198, 2197–2212.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by I:

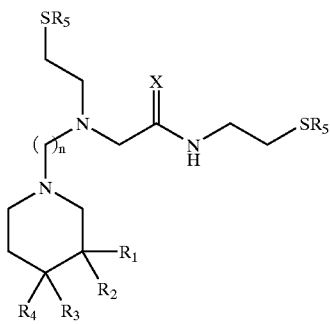

wherein

X represents O or $(H)_2$;

R represents H, alkyl, alkoxyl, alkylamino, aryl, heteroaryl, aralkyl, heteroaralkyl, acyl, alkoxycarbonyl, or alkylaminocarbonyl;

$R_1$ represents —C(O)OR;

$R_2$ represents H;

$R_3$ represents optionally substituted aryl or heteroaryl;

$R_4$ represents H;

$R_5$ represents independently for each occurrence H, alkyl, alkoxyl, alkylamino, aryl, heteroaryl, aralkyl, heteroaralkyl, acyl, alkoxycarbonyl, or alkylaminocarbonyl; and n is 1,2,3,4, or 5.

2. The compound of claim 1, wherein X represents O.
3. The compound of claim 1, wherein R represents alkyl.
4. The compound of claim 1, wherein $R_3$ represents optionally substituted phenyl.
5. The compound of claim 1, wherein $R_5$ represents H or aralkyl.
6. The compound of claim 1, wherein n is 3.
7. The compound of claim 1, wherein X represents O; and R represents alkyl.
8. The compound of claim 1, wherein X represents O; and $R_3$ represents optionally substituted phenyl.
9. The compound of claim 1, wherein X represents O; and $R_5$ represents independently for each occurrence H or aralkyl.
10. The compound of claim 1, wherein X represents O; and n is 3.
11. The compound of claim 1, wherein X represents O; R represents alkyl; and $R_3$ represents optionally substituted phenyl.
12. The compound of claim 1, wherein X represents O; R represents alkyl; and $R_5$ represents independently for each occurrence H or aralkyl.
13. The compound of claim 1, wherein X represents O; R represents alkyl; $R_3$ represents optionally substituted phenyl; and $R_5$ represents independently for each occurrence H or aralkyl.
14. The compound of claim 1, wherein X represents O; R represents methyl; $R_3$ represents 4-chlorophenyl; $R_5$ represents independently for each occurrence H or triphenylmethyl; and n is 3.

* * * * *